(12) United States Patent
Senda et al.

(10) Patent No.: US 7,652,159 B2
(45) Date of Patent: Jan. 26, 2010

(54) PROCESS FOR PRODUCING METALLOCENE COMPOUND

(75) Inventors: Taichi Senda, Takatsuki (JP); Noriyuki Hida, Sakai (JP); Hidenori Hanaoka, Suita (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 344 days.

(21) Appl. No.: 11/660,933

(22) PCT Filed: Jul. 11, 2005

(86) PCT No.: PCT/JP2005/013197

§ 371 (c)(1),
(2), (4) Date: Feb. 23, 2007

(87) PCT Pub. No.: WO2006/025159

PCT Pub. Date: Mar. 9, 2006

(65) Prior Publication Data

US 2008/0319213 A1  Dec. 25, 2008

(30) Foreign Application Priority Data

Aug. 30, 2004  (JP) .............................. 2004-249649

(51) Int. Cl.
*C07F 7/00* (2006.01)
(52) U.S. Cl. ..................................................... 556/51
(58) Field of Classification Search .................. 556/51
See application file for complete search history.

(56) References Cited

U.S. PATENT DOCUMENTS 6,329,478 B1  12/2001  Katayama et al.

FOREIGN PATENT DOCUMENTS

JP  09-087313 A  3/1997

OTHER PUBLICATIONS

Ma et al., Inorganic Chemistry Communications, 2001, 4(9), pp. 515-519.
Wang et al., Chemical Research in Chinese Universities, 2001, 17(1), pp. 115-116.
Rau et al., Journal of Organometallic Chemistry, vol. 608, pp. 71-75, 2000.

*Primary Examiner*—Porfirio Nazario Gonzalez
(74) *Attorney, Agent, or Firm*—Birch, Stewart, Kolasch & Birch, LLP

(57) ABSTRACT

The invention provides a process for producing a metallocene compound of formula (3)

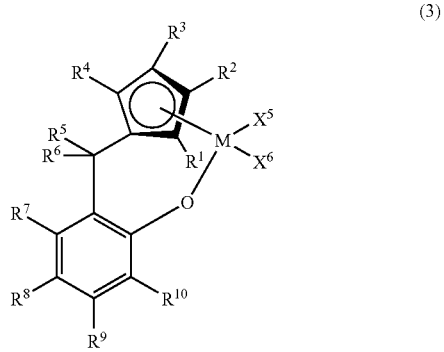

(3)

wherein $R^1$ to $R^9$ independently denote a hydrogen atom, a halogen atom, an alkyl, or the like;
$R^{10}$ denotes a halogen atom, an alkyl, an alkoxy, or the like;
$X^5$ and $X^6$ independently denote a hydrogen atom, a halogen atom, or the like; and M denotes a transition metal atom of Group 4 of the Periodic Table, which process is characterized by reacting a silicon-substituted cyclopentadiene compound of formula (1)

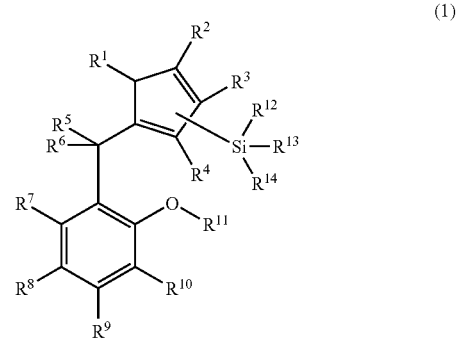

(1)

wherein $R^1$ to $R^{10}$ independently denote the same as described above; $R^{11}$ denotes a hydrocarbon group or a trisubstituted silyl; and $R^{12}$ to $R^{14}$ independently denote a halogen atom or a hydrocarbon group, with a transition metal compound of the following formula (2)

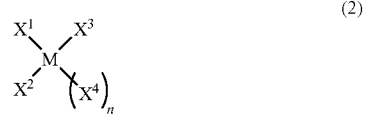

(2)

wherein M denotes the same as described above;
$X^1$, $X^2$, $X^3$, and $X^4$ independently denotes a hydrogen atom, a halogen atom, an alkyl, or the like, in a solvent containing an aromatic hydrocarbon.

7 Claims, No Drawings

PROCESS FOR PRODUCING METALLOCENE COMPOUND

TECHNICAL FIELD

The invention relates to a process for producing a metallocene compound.

BACKGROUND OF THE INVENTION

Metallocene complexes are useful as one component of polymerization catalysts to be used for olefin polymerization and a large number of metallocene complexes have been reported. Particularly, a bridged half metallocene complexes having a ligand consisting of cyclopentadiene and phenol bridged by a Group 14 atom of the Periodic Table is highly expected as a metal complexes to have unique activity owing to the unique structure among the metallocene complexes (e.g., reference to Patent Document 1). The process of producing the bridged half metallocene complexes generally involves generation of an anion from a ligand by reacting the ligand with a base and reacting the resulting anion with a metal complex precursor, however it has been desired to develop an industrially advantageous method.

Patent Document 1: Japanese Patent Application Laid-Open (JP-A) No. 9-87313

Non-Patent Document 1: J. Organomet. Chem. 2000, 608, 71-75

DISCLOSURE OF THE INVENTION

The invention relates to an improved and more advantageous process for producing a metallocene compound.

The invention provides a process for producing a metallocene compound of formula (3)

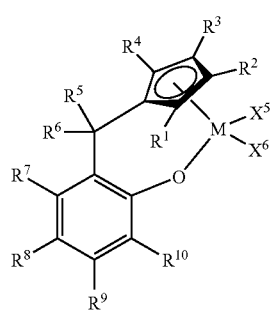

(3)

wherein $R^1$, $R^2$, $R^3$ and $R^4$ independently denote a hydrogen atom, a halogen atom, a substituted or unsubstituted $C_{1-20}$ alkyl, a substituted or unsubstituted $C_{6-20}$ aryl, or a substituted or unsubstituted $C_{7-20}$ aralkyl;

$R^5$, $R^6$, $R^7$, $R^8$, and $R^9$ independently denote a hydrogen atom, a halogen atom, a substituted or unsubstituted $C_{1-20}$ alkyl, a substituted or unsubstituted $C_{1-20}$ alkoxy, a substituted or unsubstituted $C_{6-20}$ aryl, a substituted or unsubstituted $C_{6-20}$ aryloxy, a substituted or unsubstituted $C_{7-20}$ aralkyl, a substituted or unsubstituted $C_{7-20}$ aralkyloxy, a silyl having a substituent of a substituted or unsubstituted $C_{1-20}$ hydrocarbon group, a silyloxy having a substituent of a substituted or unsubstituted $C_{1-20}$ hydrocarbon group, or an amino having a substituent of a substituted or unsubstituted $C_{1-20}$ hydrocarbon group;

$R^{10}$ denotes a halogen atom, a substituted or unsubstituted $C_{1-20}$ alkyl, a substituted or unsubstituted $C_{1-20}$ alkoxy, a substituted or unsubstituted $C_{6-20}$ aryl, a substituted or unsubstituted $C_{6-20}$ aryloxy, a substituted or unsubstituted $C_{7-20}$ aralkyl, a substituted or unsubstituted $C_{7-20}$ aralkyloxy, a silyl having a substituent of a substituted or unsubstituted $C_{1-20}$ hydrocarbon group, a silyloxy having a substituent of a substituted or unsubstituted $C_{1-20}$ hydrocarbon group, or an amino having a substituent of a substituted or unsubstituted $C_{1-20}$ hydrocarbon group;

M denotes a transition metal atom of Group 4 of the Periodic Table;

$X^5$ and $X^6$ may be same or different and independently denote a hydrogen atom, a halogen atom, a substituted or unsubstituted $C_{1-20}$ alkyl, a substituted or unsubstituted $C_{1-20}$ alkoxy, a substituted or unsubstituted $C_{6-20}$ aryl, a substituted or unsubstituted $C_{6-20}$ aryloxy, a substituted or unsubstituted $C_{7-20}$ aralkyl, a substituted or unsubstituted $C_{7-20}$ aralkyloxy, or an amino having a substituent of a substituted or unsubstituted $C_{1-20}$ hydrocarbon group; each neighboring groups of $R^1$, $R^2$, $R^3$ and $R^4$ may be optionally bonded each other to form a ring; $R^5$ and $R^6$ may be bonded to each other to form a ring; and neighboring groups of $R^7$, $R^8$, $R^9$ and $R^{10}$ may be optionally bonded each other to form a ring, which process comprises reacting a silicon-substituted cyclopentadiene compound of formula (1)

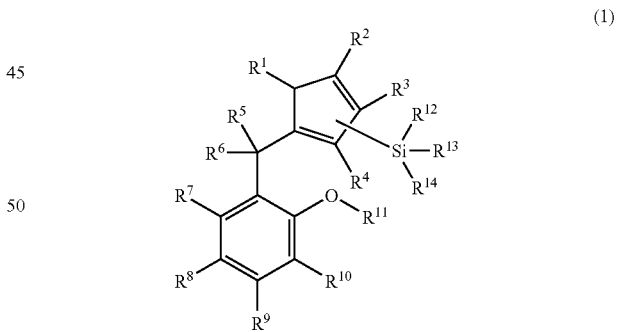

(1)

wherein $R^1$ to $R^{10}$ independently are the same as described above; $R^{11}$ denotes a substituted or unsubstituted hydrocarbon group or a tri-substituted silyl;

$R^{12}$, $R^{13}$, and $R^{14}$ independently denote a halogen atom or a substituted or unsubstituted hydrocarbon group; two or three of $R^{12}$, $R^{13}$, and $R^{14}$ may be bonded one another to form a ring; silicon may be bonded with any one of carbon atoms of the cyclopentadiene ring; and the position of the double bonds of the cyclopentadiene ring may be optional, with a transition metal compound of formula (2)

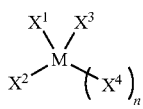

(2)

wherein M denotes the same as described above;

$X^1$, $X^2$, $X^3$, and $X^4$ may be same or different and independently denote a hydrogen atom, a halogen atom, a substituted or unsubstituted $C_{1-20}$ alkyl, a substituted or unsubstituted $C_{1-20}$ alkoxy, a substituted or unsubstituted $C_{6-20}$ aryl, a substituted or unsubstituted $C_{6-20}$ aryloxy, a substituted or unsubstituted $C_{7-20}$ aralkyl, a substituted or unsubstituted $C_{7-20}$ aralkyloxy, or an amino group substituted with a substituted or unsubstituted $C_{1-20}$ hydrocarbon group; and n denotes 0 or 1, in a solvent containing an aromatic hydrocarbon; and a process for producing a metallocene compound of formula (3)

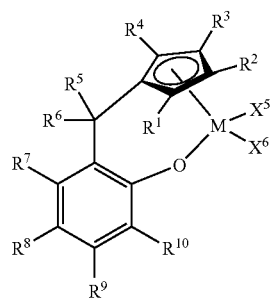

(3)

wherein $R^1$, $R^2$, $R^3$, $R^4$, $R^5$, $R^6$, $R^7$, $R^8$, $R^9$, $R^{10}$, M, $X^5$, and $X^6$ independently denote the same as described above, which process comprise reacting a substituted cyclopentadiene compound of formula (4)

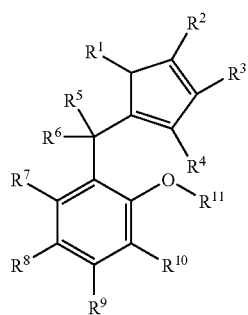

(4)

wherein $R^1$, $R^2$, $R^3$, $R^4$, $R^5$, $R^6$, $R^7$, $R^8$, $R^9$, $R^{10}$, and $R^{11}$ independently denote the same as described above, and the double bonds of the cyclopentadiene ring may be at optional positions, with a base in a solvent containing an aromatic hydrocarbon, and reacting the resulting with a silyl halide compound of formula (5)

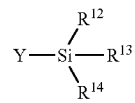

(5)

wherein $R^{12}$, $R^{13}$, and $R^{14}$ independently denote the same as described above; and Y denotes a halogen atom, and reacting the resulting compound, without refining the compound, with a transition metal compound of formula (2)

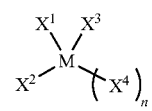

(2)

wherein M, $X^1$, $X^2$, $X^3$, $X^4$, and n independently denote the same as described above.

BEST MODE FOR CARRYING OUT THE INVENTION

Hereinafter, the invention will be described more in detail.

In compounds of the invention, a halogen atom represented by $R^1$, $R^2$, $R^3$, $R^4$, $R^5$, $R^6$, $R^7$, $R^8$, $R^9$, $R^{10}$, $R^{12}$, $R^{13}$, $R^{14}$, $X^1$, $X^2$, $X^3$, $X^4$, $X^5$, or $X^6$ include a fluorine atom, a chlorine atom, a bromine atom, and an iodine atom, and preferred is a chlorine atom.

The substituent group of the substituted $C_{1-20}$ alkyl group represented by $R^1$, $R^2$, $R^3$, $R^4$, $R^5$, $R^6$, $R^7$, $R^8$, $R^9$, $R^{10}$, $X^1$, $X^2$, $X^3$, $X^4$, $X^5$, or $X^6$ include, for example, a halogen atom such as a fluorine atom, a chlorine atom, a bromine atom, or an iodine atom. Specific examples of the substituted or unsubstituted alkyl are methyl, ethyl, n-propyl, isopropyl, n-butyl, sec-butyl, tert-butyl, n-pentyl, neopentyl, amyl, n-hexyl, heptyl, n-octyl, n-nonyl, n-decyl, n-dodecyl, n-tridecyl, tetradecyl, pentadecyl, hexadecyl, heptadecyl, octadecyl, nonadecyl, n-eicosyl, fluoromethyl, difluoromethyl, trifluoromethyl, chloromethyl, dichloromethyl, trichloromethyl, bromomethyl, dibromomethyl, tribromomethyl, iodomethyl, diiodomethyl, triiodomethyl, fluoroethyl, difluoroethyl, trifluoroethyl, tetrafluoroethyl, pentafluoroethyl, chloroethyl, dichloroethyl, trichloroethyl, tetrachloroethyl, pentachloroethyl, bromoethyl, dibromoethyl, tribromoethyl, tetrabromoethyl, pentabromoethyl, perfluoropropyl, perfluorobutyl, perfluoropentyl, perfluorohexyl, perfluorooctyl, perfluorododecyl, perfluoropentadecyl, perfluoroeicosyl, perchloropropyl, perchlorobutyl, perchloropentyl, perchlorohexyl, perchlorooctyl, perchlorododecyl, perchloropentadecyl, perchloroeicosyl, perbromopropyl, perbromobutyl, perbromopentyl, perbromohexyl, perbromooctyl, perbromododecyl, perbromopentadecyl, and perbromoeicosyl and preferred examples are methyl, ethyl, isopropyl, tert-butyl, and amyl.

Specific examples of the unsubstituted $C_{7-20}$ aralkyl represented by $R^1$, $R^2$, $R^3$, $R^4$, $R^5$, $R^6$, $R^7$, $R^8$, $R^9$, $R^{10}$, $X^1$, $X^2$, $X^3$, $X^4$, $X^5$, or $X^6$ include, benzyl, (2-methylphenyl)methyl, (3-methylphenyl)methyl, (4-methylphenyl)methyl, (2,3- dimethylphenyl)methyl, (2,4-dimethylphenyl)methyl, (2,5-dimethylphenyl)methyl, (2,6-dimethylphenyl)methyl, (3,4-dimethylphenyl)methyl, (4,6-dimethylphenyl)methyl, (2,3,4-trimethylphenyl)methyl, (2,3,5-trimethylphenyl)methyl, (2,3,6-trimethylphenyl)methyl, (3,4,5-trimethylphenyl)methyl, (2,3,6-trimethylphenyl)methyl, (2,3,4,5-tetramethylphenyl)methyl, (2,3,4,6-tetramethylphenyl)methyl, (2,3,5,6-tetramethylphenyl)methyl, (pentamethylphenyl)methyl, (ethylphenyl)methyl, (n-propylphenyl)methyl, (isopropylphenyl)methyl, (n-butylphenyl)methyl, (sec-butylphenyl)methyl, (tert-butylphenyl)methyl, (n-pentylphenyl)methyl, (neopentylphenyl)methyl, (n-hexylphenyl)methyl, (n-octylphenyl)methyl, (n-decylphenyl)methyl, (n-decylphenyl)methyl, naphthylmethyl, and anthracenylmethyl, and preferred is benzyl.

Examples of the substituted $C_{7-20}$ aralkyl include those exemplified as unsubstituted $C_{7-20}$ aralkyl groups substituted with a halogen atom such as a fluorine atom, a chlorine atom, a bromine atom, or an iodine atom as a substituent.

Specific examples of the unsubstituted $C_{6-20}$ aryl represented by $R^1, R^2, R^3, R^4, R^5, R^6, R^7, R^8, R^9, R^{10}, X^1, X^2, X^3, X^4, X^5$, or $X^6$ include phenyl, 2-tolyl, 3-tolyl, 4-tolyl, 2,3-xylyl, 2,4-xylyl, 2,5-xylyl, 2,6-xylyl, 3,4-xylyl, 3,5-xylyl, 2,3,4-trimethylphenyl, 2,3,5-trimethylphenyl, 2,3,6-trimethylphenyl, 2,4,6-trimethylphenyl, 3,4,5-trimethylphenyl, 2,3,4,5-tetramethylphenyl, 2,3,4,6-tetramethylphenyl, 2,3,5,6-tetramethylphenyl, pentamethylphenyl, ethylphenyl, n-propylphenyl, isopropylphenyl, n-butylphenyl, sec-butylphenyl, tert-butylphenyl, n-pentylphenyl, neopentylphenyl, n-hexylphenyl, n-octylphenyl, n-decylphenyl, n-dodecylphenyl, n-tetradecylphenyl, naphthyl, and anthracenyl, and preferably phenyl.

Examples of the substituted $C_{6-20}$ aryl include these exemplified as the unsubstituted $C_{6-20}$ aryl groups substituted with a halogen atom such as a fluorine atom, chlorine atom, a bromine atom, or an iodine atom as a substituent.

Specific examples of the unsubstituted $C_{1-20}$ hydrocarbon in the silyl having a substituted or unsubstituted $C_{1-20}$ hydrocarbon represented by $R^5, R^6, R^7, R^8, R^9$, or $R^{10}$ are a $C_{1-10}$ alkyl such as methyl, ethyl, n-propyl, isopropyl, n-butyl, sec-butyl, tert-butyl, isobutyl, n-pentyl, n-hexyl, cyclohexyl, n-heptyl, n-octyl, n-nonyl, or n-decyl; and an aryl such as phenyl and these substituent groups may be bonded one another to form rings.

Specific examples of the substituted silyl having the unsubstituted $C_{1-20}$ hydrocarbon as a substituent group are mono-$C_{1-20}$ hydrocarbon substituted a silyl group such as methylsilyl, ethylsilyl, and phenylsilyl; a di-$C_{1-20}$ hydrocarbon substituted silyl group such as dimethylsilyl, diethylsilyl, and diphenylsilyl; a tri-$C_{1-20}$ hydrocarbon substituted silyl such as trimethylsilyl, triethylsilyl, tri-n-propylsilyl, triisopropylsilyl, tri-n-butylsilyl, tri-sec-butylsilyl, tri-tert-butylsilyl, triisobutylsilyl, tert-butyldimethylsilyl, tri-n-pentylsilyl, tri-n-hexylsilyl, tricyclohexylsilyl, and triphenylsilyl; and a cyclic silyl having substituent groups forming a ring such as cyclotrimethylenemethylsilyl, cyclotetramethylenemethylsilyl, cyclopentamethylenemethylsilyl, cyclotrimethylenephenylsilyl, cyclotetramethylenephenylsilyl, and cyclopentamethylenephenylsilyl and preferably trimethylsilyl, tert-butyldimethylsilyl, and triphenylsilyl. Examples of the hydrocarbon group composing these substituted silyl groups may also include substituted $C_{1-20}$ hydrocarbon having, as a substituent, a halogen atom such as a fluorine atom, a chlorine atom, a bromine atom, and a iodine atom, besides the above exemplified unsubstituted hydrocarbon groups.

Specific examples of the unsubstituted $C_{1-20}$ alkoxy represented by $R^5, R^6, R^7, R^8, R^9, R^{10}, X^1, X^2, X^3, X^4, X^5$, or $X^6$ are methoxy, ethoxy, n-propoxy, isopropoxy, n-butoxy, sec-butoxy, tert-butoxy, n-pentyloxy, neopentyloxy, n-hexyloxy, n-octyloxy, n-nonyloxy, n-decyloxy, n-dodecyloxy, n-undecyloxy, n-dodecyloxy, tridecyloxy, tetradecyloxy, n-pentadecyloxy, hexadecyloxy, heptadecyloxy, octadecyloxy, nonadecyloxy, or n-eicosyloxy, and preferred are methoxy, ethoxy, and tert-butoxy.

Examples of the substituted $C_{1-20}$ alkoxy include those exemplified as unsubstituted $C_{1-20}$ alkoxy groups substituted with a halogen atom such as a fluorine atom, a chlorine atom, a bromine atom, and an iodine atom as a substituent.

Specific examples of the unsubstituted $C_{7-20}$ aralkyloxy represented by $R^5, R^6, R^7, R^8, R^9, R^{10}, X^1, X^2, X^3, X^4, X^5$, or $X^6$ are benzyloxy, (2-methylphenyl)methoxy, (3-methylphenyl)methoxy, (4-methylphenyl)methoxy, (2,3-dimethylphenyl)methoxy, (2,4-dimethylphenyl)methoxy, (2,5-dimethylphenyl)methoxy, (2,6-dimethylphenyl)methoxy, (3,4-dimethylphenyl)methoxy, (3,5-dimethylphenyl)methoxy, (2,3,4-trimethylphenyl)methoxy, (2,3,5-trimethylphenyl)methoxy, (2,3,6-trimethylphenyl)methoxy, (2,4,5-trimethylphenyl)methoxy, (2,4,6-trimethylphenyl)methoxy, (3,4,5-trimethylphenyl)methoxy, (2,3,4,5-tetramethylphenyl)methoxy, (2,3,4,6-tetramethylphenyl)methoxy, (2,3,5,6-tetramethylphenyl)methoxy, (pentamethylphenyl)methoxy, (ethylphenyl)methoxy, (n-propylphenyl)methoxy, (isopropylphenyl)methoxy, (n-butylphenyl)methoxy, (sec-butylphenyl)methoxy, (tert-butylphenyl)methoxy, (n-hexylphenyl)methoxy, (n-octylphenyl)methoxy, (n-decylphenyl)methoxy, naphthylmethoxy, and anthracenylmethoxy, and preferably benzyloxy.

Examples of the substituted $C_{7-20}$ aralkyloxy include these exemplified as the unsubstituted $C_{7-20}$ aralkyloxy groups substituted with a halogen atom such as a fluorine atom, chlorine atom, a bromine atom, or an iodine atom as a substituent.

Specific examples of the unsubstituted $C_{6-20}$ aryloxy represented by $R^5, R^6, R^7, R^8, R^9, R^{10}, X^1, X^2, X^3, X^4, X^5$, and $X^6$ include phenoxy, 2-methylphenoxy, 3-methylphenoxy, 4-methylphenoxy, 2,3-dimethylphenoxy, 2,4-dimethylphenoxy, 2,5-dimethylphenoxy, 2,6-dimethylphenoxy, 3,4-dimethylphenoxy, 3,5-dimethylphenoxy, 2,3,4-trimethylphenoxy, 2,3,5-trimethylphenoxy, 2,3,6-trimethylphenoxy, 2,4,5-trimethylphenoxy, 2,4,6-trimethylphenoxy, 3,4,5-trimethylphenoxy, 2,3,4,5-tetramethylphenoxy, 2,3,4,6-tetramethylphenoxy, 2,3,5,6-tetramethylphenoxy, pentamethylphenoxy, ethylphenoxy, n-propylphenoxy, isopropylphenoxy, n-butylphenoxy, sec-butylphenoxy, tert-butylphenoxy, n-hexylphenoxy, n-octylphenoxy, n-decylphenoxy, n-tetradecylphenoxy, naphthoxy, and anthracenoxy, and preferred is phenoxy.

Examples of the substituted $C_{6-20}$ aryloxy include those exemplified as unsubstituted $C_{6-20}$ aryloxy groups substituted with a halogen atom such as a fluorine atom, a chlorine atom, a bromine atom, and an iodine atom as a substituent.

The amino substituted with a substituted or unsubstituted $C_{1-20}$ hydrocarbon group represented by $R^5, R^6, R^7, R^8, R^9, R^{10}, X^1, X^2, X^3, X^4, X^5$ or $X^6$ is an amino group di-substituted with substituted or unsubstituted $C_{1-20}$ hydrocarbon groups, and examples of the unsubstituted $C_{1-20}$ hydrocarbon group include a $C_{1-20}$ alkyl such as methyl, ethyl, n-propyl, isopropyl, n-butyl, sec-butyl, tert-butyl, isobutyl, n-pentyl, n-hexyl, or cyclohexyl; and an aryl such as phenyl and these substituent groups may be bonded one another to form rings.

Examples of the amino group substituted with the unsubstituted $C_{1-20}$ hydrocarbon groups include dimethylamino, diethylamino, di-n-propylamino, diisopropylamine, di-n-butylamino, di-sec-butylamino, di-tert-butylamino, di-isobutylamino, tert-butylisopropylamino, di-n-hexylamino, di-n-octylamino, di-n-decylamino, diphenylamino, bistrimethylsilylamino, bis(tert-butyldimethylsilyl)amino, pyrrolyl, pyrrolidinyl, piperidinyl, carbazolyl, dihydroindolyl, and dihydroisoindolyl and preferably dimethylamino, diethylamino, pyrrolidinyl, and piperidinyl.

Examples of the substituted $C_{1-20}$ hydrocarbon group include those exemplified as $C_{1-20}$ hydrocarbon groups substituted with a halogen atom such as a fluorine atom, a chlorine atom, a bromine atom, and an iodine atom as a substituent.

The silyloxy substituted with a substituted or unsubstituted $C_{1-20}$ hydrocarbon group represented by $R^5, R^6, R^7, R^8, R^9$, or $R^{10}$ is a silyloxy group substituted with substituted or unsubstituted $C_{1-20}$ hydrocarbon groups, and examples of the unsubstituted $C_{1-20}$ hydrocarbon group include the above-exemplified $C_{1-20}$ alkyl such as methyl, ethyl, n-propyl, isopropyl, n-butyl, sec-butyl, tert-butyl, isobutyl, n-pentyl, n-hexyl, or cyclohexyl; and an aryl such as phenyl, and these substituent groups may be bonded one another to form rings.

Examples of the silyloxy group substituted with the unsubstituted $C_{1-20}$ hydrocarbon groups include trimethylsilyloxy, triethylsilyloxy, tri-n-butylsilyloxy, triphenylsilyloxy, triisopropylsilyloxy, tert-butyldimethylsilyloxy, dimethylphenylsilyloxy, and methyldiphenylsilyloxy, and preferred are trimethylsilyloxy, triphenylsilyloxy, and triisopropylsilyloxy.

Examples of the $C_{1-20}$ hydrocarbon group-substituted silyloxy are those exemplified as silyloxy groups having a halogen atom such as a fluorine atom, a chlorine atom, a bromine atom, and an iodine atom as a substituent in the above-exemplified unsubstituted $C_{1-20}$ hydrocarbon groups.

Two neighboring substituent groups among $R^1$ to $R^4$ and optional two neighboring substituent groups among $R^7$ to $R^{10}$ may be bonded each other to form rings, and $R^5$ and $R^6$ may be bonded each other to form a ring and two or three of $R^{12}$, $R^{13}$, and $R^{14}$ may be bonded to form a ring.

Examples of the rings formed by bonding two neighboring substituent groups among $R^1$ to $R^4$, two neighboring substituent groups among $R^7$ to $R^{10}$, $R^5$ and $R^6$, and two or three of $R^{12}$, $R^{13}$, and $R^{14}$ may be saturated or unsaturated hydrocarbon rings having a substituted or unsubstituted $C_{1-20}$ hydrocarbon group. Specific examples of the rings are alicyclic $C_{3-8}$ hydrocarbon rings such as cyclopropane ring, cyclobutane ring, cyclopentane ring, cycloheptane ring, or cyclooctane ring; and aromatic $C_{6-14}$ hydrocarbon rings such as benzene ring, naphthalene ring, or anthracene ring.

Examples of the unsubstituted hydrocarbon group represented by $R^{11}, R^{12}, R^{13}$, and $R^{14}$ include an $C_{1-10}$ alkyl such as methyl, ethyl, propyl, butyl, pentyl, hexyl, heptyl, octyl, nonyl, or decyl; an $C_{2-10}$ alkenyl such as vinyl, aryl, propenyl, 2-methyl-2-propenyl, homoallyl, pentenyl, hexenyl, heptenyl, octenyl, nonenyl, or decenyl; and an $C_{7-12}$ aralkyl such as benzyl, (4-methylphenyl)methyl, and (2,4,6-trimethylphenyl)methyl.

Examples of the substituted hydrocarbon include an alkyl substituted with an alkoxy or alkoxyalkyl such as methoxymethyl or methoxyethoxymethyl, and also hydrocarbon groups derived from the above-exemplified hydrocarbon groups by substituting a halogen atom for hydrogen, and specific examples of halogen-substituted hydrocarbon groups include 2-chloro-2-propenyl.

Examples of the tri-substituted silyl represented by $R^{11}$ include trimethylsilyl, triethylsilyl, tri-n-propylsilyl, triisopropylsilyl, tri-n-butylsilyl, tri-sec-butylsilyl, tri-tert-butylsilyl, triisobutylsilyl, tert-butyldimethylsilyl, tri-n-pentylsilyl, tri-n-hexylsilyl, tricyclohexylsilyl, and triphenylsilyl.

Among the examples of $R^{11}$, the alkyl is preferable and methyl is more preferable in that the metallocene compound of formula (3) is produced in a higher yield.

Examples of the silicon-substituted cyclopentadiene compound of formula (1) of the invention include 1-methoxy-2-[1-(3-trimethylsilyl-cyclopenta-1,4-dienyl)-1-methyl-ethyl]benzene, 1-methoxy-4,6-dimethyl-2-[1-(3-trimethylsilyl-cyclopenta-1,4-dienyl)-1-methyl-ethyl]benzene, 6-tert-butyl-1-methoxy-4-methyl-2-[1-(3-trimethylsilyl-cyclopenta-1,4-dienyl)-1-methyl-ethyl]benzene, 1-methoxy-2-phenyl-6-[1-(3-trimethylsilyl-cyclopenta-1,4-dienyl)-1-methyl-ethyl]benzene, 1-tert-butyldimethylsilyl-2-methoxy-5-methyl-3-[1-(3-trimethylsilyl-cyclopenta-1,4-dienyl)-1-methyl-ethyl]benzene, 2-methoxy-5-methyl-1-trimethylsilyl-3-[1-(3-trimethylsilyl-cyclopenta-1,4-dienyl)-1-methyl-ethyl]benzene, 6-tert-butyl-1,4-dimethoxy-2-[1-(3-trimethylsilyl-cyclopenta-1,4-dienyl)-1-methyl-ethyl]benzene, 5-tert-butyl-1-chloro-4-methoxy-3-[1-(3-trimethylsilyl-cyclopenta-1,4-dienyl)-1-methyl-ethyl]benzene, 6-tert-butyl-1-methoxy-2-[1-(3-trimethylsilyl-cyclopenta-1,4-dienyl)-1-methyl-ethyl]benzene, and isomers of these exemplified compounds which isomers have the double bond of the cyclopentadiene ring at different positions and isomers of these exemplified compounds which isomers have the trimethylsilyl group at a different position of the cyclopentadiene ring;

1-methoxy-2-[1-(4-methyl-3-trimethylsilyl-cyclopenta-1,4-dienyl)-1-methyl-ethyl]benzene, 1-methoxy-4,6-dimethyl-2-[1-(4-methyl-3-trimethylsilyl-cyclopenta-1,4-dienyl)-1-methyl-ethyl]benzene, 6-tert-butyl-1-methoxy-4-methyl-2-[1-(4-methyl-3-trimethylsilyl-cyclopenta-1,4-dienyl)-1-methyl-ethyl]benzene, 1-methoxy-2-phenyl-6-[1-(4-methyl-3-trimethylsilyl-cyclopenta-1,4-dienyl)-1-methyl-ethyl]benzene, 1-tert-butyldimethylsilyl-2-methoxy-5-methyl-3-[1-(4-methyl-3-trimethylsilyl-cyclopenta-1,4-dienyl)-1-methyl-ethyl)]benzene, 2-methoxy-5-methyl-1-trimethylsilyl-3-[1-(4-methyl-3-trimethylsilyl-cyclopenta-1,4-dienyl)-1-methyl-ethyl]benzene, 6-tert-butyl-1,4-dimethoxy-2-[1-(4-methyl-3-trimethylsilyl-cyclopenta-1,4-dienyl)-1-methyl-ethyl]benzene, 5-tert-butyl-1-chloro-4-methoxy-3-[1-(4-methyl-3-trimethylsilyl-cyclopenta-1,4-dienyl)-1-methyl-ethyl]benzene, 6-tert-butyl-1-methoxy-2-[1-(4-methyl-3-trimethylsilyl-cyclopenta-1,4-dienyl)-1-methyl-ethyl]benzene, and isomers of these exemplified compounds which isomers have the double bond of the cyclopentadiene ring at different positions and isomers of these exemplified compounds which isomers have the trimethylsilyl group at a different position of the cyclopentadiene ring;

1-methoxy-2-[1-(3-trimethylsilyl-cyclopenta-1,4-dienyl)-1-ethyl-propyl]benzene, 1-methoxy-4,6-dimethyl-2-[1-(3-trimethylsilyl-cyclopenta-1,4-dienyl)-1-ethyl-propyl]benzene, 6-tert-butyl-1-methoxy-4-methyl-2-[1-(3-trimethylsilyl-cyclopenta-1,4-dienyl)-1-ethyl-propyl]benzene, 1-methoxy-2-phenyl-6-[1-(3-trimethylsilyl-cyclopenta-1,4-dienyl)-1-ethyl-propyl]benzene, 1-tert-butyldimethylsilyl-2-methoxy-5-methyl-3-[1-(3-trimethylsilyl-cyclopenta-1,4-dienyl)-1-ethyl-propyl]benzene, 2-methoxy-5-methyl-1-trimethylsilyl-3-[1-(3-trimethylsilyl-cyclopenta-1,4-dienyl)-1-ethyl-propyl]benzene, 6-tert-butyl-1,4-dimethoxy-2-[1-(3-trimethylsilyl-cyclopenta-1,4-dienyl)-1-ethyl-propyl]benzene, 5-tert-butyl-1-chloro-4-methoxy-3-[1-(3-trimethylsilyl-cyclopenta-1,4-dienyl)-1-ethyl-propyl]benzene, 6-tert-butyl-1-methoxy-2-[1-(3-trimethylsilyl-cyclopenta-1,4-dienyl)-1-ethyl-propyl]benzene, and isomers of these exemplified compounds which isomers have the double bond of the cyclopentadiene ring is at different positions and isomers of these exemplified compounds which isomers have the trimethylsilyl group at a different position of the cyclopentadiene ring;

1-methoxy-2-[1-(3-trimethylsilyl-cyclopenta-1,4-dienyl)-1-cyclopentyl]benzene, 1-methoxy-4,6-dimethyl-2-[1-(3-trimethylsilyl-cyclopenta-1,4-dienyl)-1-cyclopentyl]benzene, 6-tert-butyl-1-methoxy-4-methyl-2-[1-(3-trimethylsilyl-cyclopenta-1,4-dienyl)-1-cyclopentyl]benzene, 1-methoxy-2-phenyl-6-[1-(3-trimethylsilyl-cyclopenta-1,4-dienyl)-1-cyclopentyl]benzene, 1-tert-butyldimethylsilyl-2-methoxy-5-methyl-3-[1-(3-trimethylsilyl-cyclopenta-1,4-dienyl)-1-cyclopentyl]benzene, 2-methoxy-5-methyl-1-trimethylsilyl-3-[1-(3-trimethylsilyl-cyclopenta-1,4-dienyl)-1-cyclopentyl]benzene, 6-tert-butyl-1,4-dimethoxy-2-[1-(3-trimethylsilyl-cyclopenta-1,4-dienyl)-1-cyclopentyl]benzene, 5-tert-butyl-1-chloro-4-methoxy-3-[1-(3-trimethylsilyl-cyclopenta-1,4-dienyl)-1-cyclopentyl]benzene, 6-tert-butyl-1-methoxy-2-[1-(3-trimethylsilyl-cyclopenta-1,4-dienyl)-1-cyclopentyl]benzene, and isomers of these exemplified compounds, which isomers have the double bond of the cyclopentadiene ring at different positions and isomers of these exemplified compounds, which isomers have the trimethylsilyl group at a different position of the cyclopentadiene ring;

1-methoxy-2-[1-(3-trimethylsilyl-cyclopenta-1,4-dienyl)-2,2-dimethylpropyl]benzene, 1-methoxy-4,6-dimethyl-2-[1-(3-trimethylsilyl-cyclopenta-1,4-dienyl)-2,2-dimethylpropyl]benzene, 6-tert-butyl-1-methoxy-4-methyl-2-[1-(3-trimethylsilyl-cyclopenta-1,4-dienyl)-2,2-dimethylpropyl]benzene, 1-methoxy-2-phenyl-6-[1-(3-trimethylsilyl-cyclopenta-1,4-dienyl)-2,2-dimethylpropyl]benzene, 1-tert-butyldimethylsilyl-2-methoxy-5-methyl-3-[1-(3-trimethylsilyl-cyclopenta-1,4-dienyl)-2,2-dimethylpropyl]benzene, 2-methoxy-5-methyl-1-trimethylsilyl-3-[1-(3-trimethylsilyl-cyclopenta-1,4-dienyl)-2,2-dimethylpropyl]benzene, 6-tert-butyl-1,4-dimethoxy-2-[1-(3-trimethylsilyl-cyclopenta-1,4-dienyl)-2,2-dimethylpropyl]benzene, 5-tert-butyl-1-chloro-4-methoxy-3-[1-(3-trimethylsilyl-cyclopenta-1,4-dienyl)-2,2-dimethylpropyl]benzene, 6-tert-butyl-1-methoxy-2-[1-(3-trimethylsilyl-cyclopenta-1,4-dienyl)-2,2-dimethylpropyl]benzene, and isomers of these exemplified compounds which isomers have the double bond of the cyclopentadiene ring at different positions and isomers of these exemplified compounds which isomers have the trimethylsilyl group at a different position of the cyclopentadiene ring;

1-methoxy-2-[1-(3-tert-butyldimethylsilyl-cyclopenta-1,4-dienyl)-1-methyl-ethyl]benzene, 1-methoxy-4,6-dimethyl-2-[1-(3-tert-butyldimethylsilyl-cyclopenta-1,4-dienyl)-1-methyl-ethyl]benzene, 6-tert-butyl-1-methoxy-4-methyl-2-[1-(3-tert-butyldimethylsilyl-cyclopenta-1,4-dienyl)-1-methyl-ethyl]benzene, 1-methoxy-2-phenyl-6-[1-(3-tert-butyldimethylsilyl-cyclopenta-1,4-dienyl)-1-methyl-ethyl]benzene, 1-tert-butyldimethylsilyl-2-methoxy-5-methyl-3-[1-(3-tert-butyldimethylsilyl-cyclopenta-1,4-dienyl)-1-methyl-ethyl]benzene, 2-methoxy-5-methyl-1-trimethylsilyl-3-[1-(3-tert-butyldimethylsilyl-cyclopenta-1,4-dienyl)-1-methyl-ethyl]benzene, 6-tert-butyl-1,4-dimethoxy-2-[1-(3-tert-butyldimethylsilyl-cyclopenta-1,4-dienyl)-1-methyl-ethyl]benzene, 5-tert-butyl-1-chloro-4-methoxy-3-[1-(3-tert-butyldimethylsilyl-cyclopenta-1,4-dienyl)-1-methyl-ethyl]benzene, 6-tert-butyl-1-methoxy-2-[1-(3-tert-butyldimethylsilyl-cyclopenta-1,4-dienyl)-1-methyl-ethyl]benzene, and isomers of these exemplified compounds which isomers have the double bond of the cyclopentadiene ring at different positions and isomers of these exemplified compounds which isomers have the trimethylsilyl group at a different position of the cyclopentadiene ring;

1-methoxy-2-[1-(9-trimethylsilyl-fluorenyl)-1-methyl-ethyl]benzene, 1-methoxy-4,6-dimethyl-2-[1-(9-trimethylsilyl-fluorenyl)-1-methyl-ethyl]benzene, 6-tert-butyl-1-methoxy-4-methyl-2-[1-(9-trimethylsilyl-fluorenyl)-1-methyl-ethyl]benzene, 1-methoxy-2-phenyl-6-[1-(9-trimethylsilyl-fluorenyl)-1-methyl-ethyl]benzene, 1-tert-butyldimethylsilyl-2-methoxy-5-methyl-3-[1-(9-trimethylsilyl-fluorenyl)-1-methyl-ethyl]benzene, 2-methoxy-5-methyl-1-trimethylsilyl-3-[1-(9-trimethylsilyl-fluorenyl)-1-methyl-ethyl]benzene, 6-tert-butyl-1,4-dimethoxy-2-[1-(9-trimethylsilyl-fluorenyl)-1-methyl-ethyl]benzene, 5-tert-butyl-1-chloro-4-methoxy-3-[1-(9-trimethylsilyl-fluorenyl)-1-methyl-ethyl]benzene, 6-tert-butyl-1-methoxy-2-[1-(9-trimethylsilyl-fluorenyl)-1-methyl-ethyl]benzene, and isomers of these exemplified compounds which isomers have the double bond of the fluorene ring at different positions and isomers of these exemplified compounds which isomers have the trimethylsilyl group bonded with the fluorene ring at a different position;

1-methoxy-2-[1-(1-trimethylsilyl-indenyl)-1-methyl-ethyl]benzene, 1-methoxy-4,6-dimethyl-2-[1-(1-trimethylsilyl-indenyl)-1-methyl-ethyl]benzene, 6-tert-butyl-1-methoxy-4-methyl-2-[1-(1-trimethylsilyl-indenyl)-1-methyl-ethyl]benzene, 1-methoxy-2-phenyl-6-[1-(1-trimethylsilyl-indenyl)benzene, 1-tert-butyldimethylsilyl-2-methoxy-5-methyl-3-[1-(1-trimethylsilyl-indenyl)-1-methyl-ethyl]benzene, 2-methoxy-5-methyl-1-trimethylsilyl-3-[1-(1-trimethylsilyl-indenyl)-1-methyl-ethyl]benzene, 6-tert-butyl-1,4-dimethoxy-2-[1-(1-trimethylsilyl-indenyl)-1-methyl-ethyl]benzene, 5-tert-butyl-1-chloro-4-methoxy-3-[1-(1-trimethylsilyl-indenyl)-1-methyl-ethyl]benzene, 6-tert-butyl-1-methoxy-2-[1-(1-trimethylsilyl-indenyl)-1-methyl-ethyl]benzene, and isomers of these exemplified compounds which isomers have the double bond of the indenyl ring at different positions and isomers of these exemplified compounds which isomers have the trimethylsilyl group bonded with the indenyl ring at a different position; and compounds obtained by replacing methoxy of these exemplified compounds with ethoxy, isopropoxy, benzoyloxy, trimethylsilyloxy, tert-butyldimethylsilyloxy, or methoxymethoxy.

Silicon of the silicon-substituted cyclopentadiene compound of formula (1) of the invention may be bonded to any carbon atom of the cyclopentadiene ring and double bond of the cyclopentadiene ring may be at any position. For example, the following substituting styles for cyclopentadiene and silicon can be exemplified and the silicon-substituted cyclopentadiene compound of the invention may be a mixture of any of these substituted compounds.

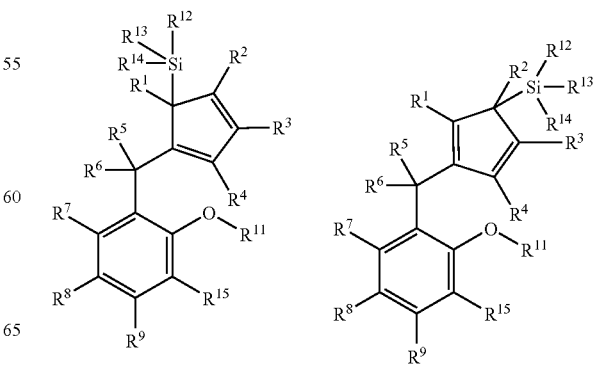

-continued

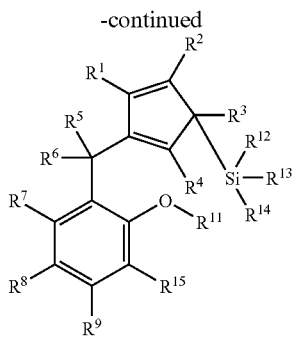

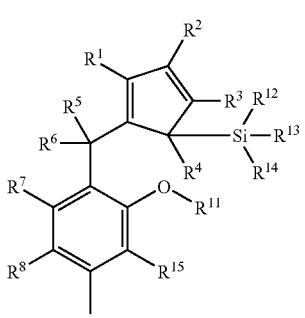

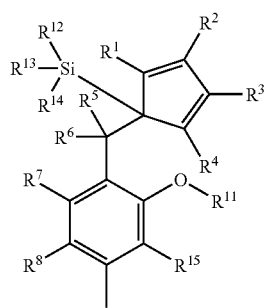

The silicon-substituted cyclopentadiene compound of formula (1) of the invention can be produced by, for example, a process which comprises reacting a substituted cyclopentadiene compound of formula (4)

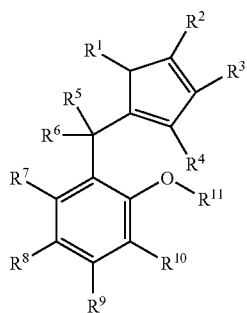

(4)

wherein $R^1$, $R^2$, $R^3$, $R^4$, $R^5$, $R^6$, $R^7$, $R^8$, $R^9$, $R^{10}$, and $R^{11}$ independently denote the same as described above, and the double bond of the cyclopentadiene may be at any position, with a base and successively reacting the resulting product with a halogenated silyl compound of formula (5)

(5)

wherein $R^{12}$, $R^{13}$, and $R^{14}$ independently denote same as described above and Y denote a halogen atom, reference to Non-Patent Document 1.

Example of the transition metal compound of formula (2) are a titanium halide such as titanium tetrachloride, titanium trichloride, titanium tetrabromide, and titanium tetraiodide; amido titanium such as tetrakis(dimethylamino)titanium, dichlorobis(dimethylamino)titanium, trichloro(dimethylamino)titanium, or tetrakis(diethylamino)titanium; an alkoxytitanium such as tetraisopropoxytitanium, tetra(n-butoxy)titanium, dichlorodiisopropoxytitanium, or trichloroisopropoxytitanium; and compounds obtained by replacing titanium of the above-mentioned-respective compounds with zirconium, or hafnium, and preferred is titanium tetrachloride. The amount of the transition metal compound is generally 0.8 mole or higher, preferably 1 mole or higher, and further preferably 1.1 moles or higher per mole of the silicon-substituted cyclopentadiene compound of formula (2) or the substituted cyclopentadiene compound of formula (4) and the upper limit is not particularly limited, however it is generally about 3 moles and preferably about 2 moles.

Examples of the metallocene compound of formula (3) include methylene(cyclopentadienyl)(3,5-dimethyl-2-phenoxy)titanium dichloride, methylene(cyclopentadienyl)(3-tert-butyl-2-phenoxy)titanium dichloride, methylene(cyclopentadienyl)(3-tert-butyl-5-methyl-2-phenoxy)titanium dichloride, methylene(cyclopentadienyl)(3-phenyl-2-phenoxy)titanium dichloride, methylene(cyclopentadienyl)(3-tert-butyldimethylsilyl-5-methyl-2-phenoxy)titanium dichloride, methylene(cyclopentadienyl)(3-trimethylsilyl-5-methyl-2-phenoxy)titanium dichloride, methylene(cyclopentadienyl)(3-tert-butyl-5-methoxy-2-phenoxy)titanium dichloride, methylene(cyclopentadienyl)(3-tert-butyl-5-chloro-2-phenoxy)titanium dichloride, methylene(methylcyclopentadienyl)(3,5-dimethyl-2-phenoxy)titanium dichloride, methylene(methylcyclopentadienyl)(3-tert-butyl-2-phenoxy)titanium dichloride, methylene (methylcyclopentadienyl)(3-tert-butyl-5-methyl-2-phenoxy) titanium dichloride, methylene(methylcyclopentadienyl)(3-phenyl-2-phenoxy)titanium dichloride, methylene (methylcyclopentadienyl)(3-tert-butyldimethylsilyl-5-methyl-2-phenoxy)titanium dichloride, methylene (methylcyclopentadienyl)(3-trimethylsilyl-5-methyl-2-phenoxy)titanium dichloride, methylene (methylcyclopentadienyl)(3-tert-butyl-5-methoxy-2-phenoxy)titanium dichloride, methylene (methylcyclopentadienyl)(3-tert-butyl-5-chloro-2-phenoxy) titanium dichloride, methylene(tert-butylcyclopentadienyl)(3,5-dimethyl-2-phenoxy)titanium dichloride, methylene(tert-butylcyclopentadienyl)(3-tert-butyl-2-phenoxy)titanium dichloride, methylene(tert-butylcyclopentadienyl)(3-tert-butyl-5-methyl-2-phenoxy)titanium dichloride, methylene(tert-butylcyclopentadienyl)(3-phenyl-2-phenoxy)titanium dichloride, methylene(tert-butylcyclopentadienyl)(3-tert-butyldimethylsilyl-5-methyl-2-phenoxy)titanium dichloride, methylene(tert-butylcyclopentadienyl)(3-trimethylsilyl-5- methyl-2-phenoxy)titanium dichloride, methylene(tert-butylcyclopentadienyl)(3-tert-butyl-5-methoxy-2-phenoxy)titanium dichloride, methylene(tert-butylcyclopentadienyl)(3-tert-butyl-5-chloro-2-phenoxy)titanium dichloride, methylene(tetramethylcyclopentadienyl)(3,5-dimethyl-2-phenoxy)titanium dichloride, methylene(tetramethylcyclopentadienyl)(3-tert-butyl-2-phenoxy)titanium dichloride, methylene(tetramethylcyclopentadienyl)(3-tert-butyl-5-methyl-2-phenoxy)titanium dichloride, methylene(tetramethylcyclopentadienyl)(3-phenyl-2-phenoxy)titanium dichloride, methylene(tetramethylcyclopentadienyl)(3-tert-butyldimethylsilyl-5-methyl-2-phenoxy)titanium dichloride, methylene(tetramethylcyclopentadienyl)(3-trimethylsilyl-5-methyl-2-phenoxy)titanium dichloride, methylene(tetramethylcyclopentadienyl)(3-tert-butyl-5-methoxy-2-phenoxy)titanium dichloride, methylene(tetramethylcyclopentadienyl)(3-tert-butyl-5-chloro-2-phenoxy)titanium dichloride, methylene(indenyl)(3,5-dimethyl-2-phenoxy)titanium dichloride, methylene(indenyl)(3-tert-butyl-2-phenoxy)titanium dichloride, methylene(indenyl)(3-tert-butyl-5-methyl-2-phenoxy)titanium dichloride, methylene(indenyl)(3-phenyl-2-phenoxy)titanium dichloride, methylene(indenyl)(3-tert-butyldimethylsilyl-5-methyl-2-phenoxy)titanium dichloride, methylene(indenyl)(3-trimethylsilyl-5-methyl-2-phenoxy)titanium dichloride, methylene(indenyl)(3-tert-butyl-5-methoxy-2-phenoxy)titanium dichloride, methylene(indenyl)(3-tert-butyl-5-chloro-2-phenoxy)titanium dichloride, methylene(fluorenyl)(3,5-dimethyl-2-phenoxy)titanium dichloride, methylene(fluorenyl)(3-tert-butyl-2-phenoxy)titanium dichloride, methylene(fluorenyl)(3-tert-butyl-5-methyl-2-phenoxy)titanium dichloride, methylene(fluorenyl)(3-phenyl-2-phenoxy)titanium dichloride, methylene(fluorenyl)(3-tert-butyldimethylsilyl-5-methyl-2-phenoxy)titanium dichloride, methylene(fluorenyl)(3-trimethylsilyl-5-methyl-2-phenoxy)titanium dichloride, methylene(fluorenyl)(3-tert-butyl-5-methoxy-2-phenoxy)titanium dichloride, methylene(fluorenyl)(3-tert-butyl-5-chloro-2-phenoxy)titanium dichloride, isopropylidene(cyclopentadienyl)(3,5-dimethyl-2-phenoxy)titanium dichloride, isopropylidene(cyclopentadienyl)(3-tert-butyl-2-phenoxy)titanium dichloride, isopropylidene(cyclopentadienyl)(3-tert-butyl-5-methyl-2-phenoxy)titanium dichloride, isopropylidene(cyclopentadienyl)(3-phenyl-2-phenoxy)titanium dichloride, isopropylidene(cyclopentadienyl)(3-tert-butyldimethylsilyl-5-methyl-2-phenoxy)titanium dichloride, isopropylidene(cyclopentadienyl)(3-trimethylsilyl-5-methyl-2-phenoxy)titanium dichloride, isopropylidene(cyclopentadienyl)(3-tert-butyl-5-methoxy-2-phenoxy)titanium dichloride, isopropylidene(cyclopentadienyl)(3-tert-butyl-5-chloro-2-phenoxy)titanium dichloride, isopropylidene(methylcyclopentadienyl)(3,5-dimethyl-2-phenoxy)titanium dichloride, isopropylidene(methylcyclopentadienyl)(3-tert-butyl-2-phenoxy)titanium dichloride, isopropylidene(methylcyclopentadienyl)(3-tert-butyl-5-methyl-2-phenoxy)titanium dichloride, isopropylidene(methylcyclopentadienyl)(3-phenyl-2-phenoxy)titanium dichloride, isopropylidene(methylcyclopentadienyl)(3-tert-butyldimethylsilyl-5-methyl-2-phenoxy)titanium dichloride, isopropylidene(methylcyclopentadienyl)(3-trimethylsilyl-5-methyl-2-phenoxy)titanium-dichloride, isopropylidene(methylcyclopentadienyl)(3-tert-butyl-5-methoxy-2-phenoxy)titanium dichloride, isopropylidene(methylcyclopentadienyl)(3-tert-butyl-5-chloro-2-phenoxy)titanium dichloride, isopropylidene(tert-butylcyclopentadienyl)(3,5-dimethyl-2-phenoxy)titanium dichloride, isopropylidene(tert-butylcyclopentadienyl)(3-tert-butyl-2-phenoxy)titanium dichloride, isopropylidene(tert-butylcyclopentadienyl)(3-tert-butyl-5-methyl-2-phenoxy)titanium dichloride, isopropylidene(tert-butylcyclopentadienyl)(3-phenyl-2-phenoxy)titanium dichloride, isopropylidene(tert-butylcyclopentadienyl)(3-tert-butyldimethylsilyl-5-methyl-2-phenoxy)titanium dichloride, isopropylidene(tert-butylcyclopentadienyl)(3-trimethylsilyl-5-methyl-2-phenoxy)titanium dichloride, isopropylidene(tert-butylcyclopentadienyl)(3-tert-butyl-5-methoxy-2-phenoxy)titanium dichloride, isopropylidene(tert-butylcyclopentadienyl)(3-tert-butyl-5-chloro-2-phenoxy)titanium dichloride, isopropylidene(tetramethylcyclopentadienyl)(3,5-dimethyl-2-phenoxy)titanium dichloride, isopropylidene(tetramethylcyclopentadienyl)(3-tert-butyl-2-phenoxy)titanium dichloride, isopropylidene(tetramethylcyclopentadienyl)(3-tert-butyl-5-methyl-2-phenoxy)titanium dichloride, isopropylidene(tetramethylcyclopentadienyl)(3-phenyl-2-phenoxy)titanium dichloride, isopropylidene(tetramethylcyclopentadienyl)(3-tert-butyldimethylsilyl-5-methyl-2-phenoxy)titanium dichloride, isopropylidene(tetramethylcyclopentadienyl)(3-trimethylsilyl-5-methyl-2-phenoxy)titanium dichloride, isopropylidene(tetramethylcyclopentadienyl)(3-tert-butyl-5-methoxy-2-phenoxy)titanium dichloride, isopropylidene(tetramethylcyclopentadienyl)(3-tert-butyl-5-chloro-2-phenoxy)titanium dichloride, isopropylidene(indenyl)(3,5-dimethyl-2-phenoxy)titanium dichloride, isopropylidene(indenyl)(3-tert-butyl-2-phenoxy)titanium dichloride, isopropylidene(indenyl)(3-tert-butyl-5-methyl-2-phenoxy)titanium dichloride, isopropylidene(indenyl)(3-phenyl-2-phenoxy)titanium dichloride, isopropylidene(indenyl)(3-tert-butyldimethylsilyl-5-methyl-2-phenoxy)titanium dichloride, isopropylidene(indenyl)(3-trimethylsilyl-5-methyl-2-phenoxy)titanium dichloride, isopropylidene(indenyl)(3-tert-butyl-5-methoxy-2-phenoxy)titanium dichloride, isopropylidene(indenyl)(3-tert-butyl-5-chloro-2-phenoxy)titanium dichloride, isopropylidene(fluorenyl)(3,5-dimethyl-2-phenoxy)titanium dichloride, isopropylidene(fluorenyl)(3-tert-butyl-2-phenoxy)titanium dichloride, isopropylidene(fluorenyl)(3-tert-butyl-5-methyl-2-phenoxy)titanium dichloride, isopropylidene(fluorenyl)(3-phenyl-2-phenoxy)titanium dichloride, isopropylidene(fluorenyl)(3-tert-butyldimethylsilyl-5-methyl-2-phenoxy)titanium dichloride, isopropylidene(fluorenyl)(3-trimethylsilyl-5-methyl-2-phenoxy)titanium dichloride, isopropylidene(fluorenyl)(3-tert-butyl-5-methoxy-2-phenoxy)titanium dichloride, isopropylidene(fluorenyl)(3-tert-butyl-5-chloro-2-phenoxy)titanium dichloride, diethylmethylene(cyclopentadienyl)(3,5-dimethyl-2-phenoxy)titanium dichloride, diethylmethylene(cyclopentadienyl)(3-tert-butyl-2-phenoxy)titanium dichloride, diethylmethylene(cyclopentadienyl)(3-tert-butyl-5-methyl-2-phenoxy)titanium dichloride, diethylmethylene(cyclopentadienyl)(3-phenyl-2-phenoxy)titanium dichloride, diethylmethylene(cyclopentadienyl)(3-tert-butyldimethylsilyl-5-methyl-2-phenoxy)titanium dichloride, diethylmethylene(cyclopentadienyl)(3-trimethylsilyl-5-methyl-2-phenoxy)titanium dichloride, diethylmethylene(cyclopentadienyl)(3-tert-butyl-5-methoxy-2-phenoxy)titanium dichloride, diethylmethylene(cyclopentadienyl)(3-tert-butyl-5-chloro-2-phenoxy)titanium dichloride, diethylmethylene(methylcyclopentadienyl)(3,5-dimethyl-2-phenoxy)titanium dichloride, diethylmethylene(methylcyclopentadienyl)(3-tert-butyl-2-phenoxy)titanium dichloride, diethylmethylene(methylcyclopentadienyl)(3-tert-butyl-5-methyl-2-phenoxy)titanium dichloride, diethylmethylene(methylcyclopentadienyl)(3-phenyl-2-phenoxy)titanium dichloride, diethylmethylene(methylcyclopentadienyl)(3-tert-butyldimethylsilyl-5-methyl-2-phenoxy)titanium dichloride, diethylmethylene(methylcyclopentadienyl)(3-trimethylsilyl-5-methyl-2-phenoxy)titanium dichloride, diethylmethylene(methylcyclopentadienyl)(3-tert-butyl-5-methoxy-2-phenoxy)titanium dichloride, diethylmethylene(methylcyclopentadienyl)(3-tert-butyl-5-chloro-2-phenoxy)titanium dichloride, diethylmethylene(tert-butylcyclopentadienyl)(3,5-dimethyl-2-phenoxy)titanium dichloride, diethylmethylene(tert-butylcyclopentadienyl)(3-tert-butyl-2-phenoxy)titanium dichloride, diethylmethylene(tert-butylcyclopentadienyl)(3-tert-butyl-5-methyl-2-phenoxy)titanium dichloride, diethylmethylene(tert-butylcyclopentadienyl)(3-phenyl-2-phenoxy)titanium dichloride, diethylmethylene(tert-butylcyclopentadienyl)(3-tert-butyldimethylsilyl-5-methyl-2-phenoxy)titanium dichloride, diethylmethylene(tert-butylcyclopentadienyl)(3-trimethylsilyl-5-methyl-2-phenoxy)titanium dichloride, diethylmethylene(tert-butylcyclopentadienyl)(3-tert-butyl-5-methoxy-2-phenoxy)titanium dichloride, diethylmethylene(tert-butylcyclopentadienyl)(3-tert-butyl-5-chloro-2-phenoxy)titanium dichloride, diethylmethylene(tetramethylcyclopentadienyl)(3,5-dimethyl-2-phenoxy)titanium dichloride, diethylmethylene(tetramethylcyclopentadienyl)(3-tert-butyl-2-phenoxy)titanium dichloride, diethylmethylene(tetramethylcyclopentadienyl)(3-tert-butyl-5-methyl-2-phenoxy)titanium dichloride, diethylmethylene(tetramethylcyclopentadienyl)(3-phenyl-2-phenoxy)titanium dichloride, diethylmethylene(tetramethylcyclopentadienyl)(3-tert-butyldimethylsilyl-5-methyl-2-phenoxy)titanium dichloride, diethylmethylene(tetramethylcyclopentadienyl)(3-trimethylsilyl-5-methyl-2-phenoxy)titanium dichloride, diethylmethylene(tetramethylcyclopentadienyl)(3-tert-butyl-5-methoxy-2-phenoxy)titanium dichloride, diethylmethylene(tetramethylcyclopentadienyl)(3-tert-butyl-5-chloro-2-phenoxy)titanium dichloride, diethylmethylene(indenyl)(3,5-dimethyl-2-phenoxy)titanium dichloride, diethylmethylene(indenyl)(3-tert-butyl-2-phenoxy)titanium dichloride, diethylmethylene(indenyl)(3-tert-butyl-5-methyl-2-phenoxy)titanium dichloride, diethylmethylene(indenyl)(3-phenyl-2-phenoxy)titanium dichloride, diethylmethylene(indenyl)(3-tert-butyldimethylsilyl-5-methyl-2-phenoxy)titanium dichloride, diethylmethylene(indenyl)(3-trimethylsilyl-5-methyl-2-phenoxy)titanium dichloride, diethylmethylene(indenyl)(3-tert-butyl-5-methoxy-2-phenoxy)titanium dichloride, diethylmethylene(indenyl)(3-tert-butyl-5-chloro-2-phenoxy)titanium dichloride, diethylmethylene(fluorenyl)(3,5-dimethyl-2-phenoxy)titanium dichloride, diethylmethylene(fluorenyl)(3-tert-butyl-2-phenoxy)titanium dichloride, diethylmethylene(fluorenyl)(3-tert-butyl-5-methyl-2-phenoxy)titanium dichloride, diethylmethylene(fluorenyl)(3-phenyl-2-phenoxy)titanium dichloride, diethylmethylene(fluorenyl)(3-tert-butyldimethylsilyl-5-methyl-2-phenoxy)titanium dichloride, diethylmethylene(fluorenyl)(3-trimethylsilyl-5-methyl-2-phenoxy)titanium dichloride, diethylmethylene(fluorenyl)(3-tert-butyl-5-methoxy-2-phenoxy)titanium dichloride, diethylmethylene(fluorenyl)(3-tert-butyl-5-chloro-2-phenoxy)titanium dichloride, diphenylmethylene(cyclopentadienyl)(3,5-dimethyl-2-phenoxy)titanium dichloride, diphenylmethylene(cyclopentadienyl)(3-tert-butyl-2-phenoxy)titanium dichloride, diphenylmethylene(cyclopentadienyl)(3-tert-butyl-5-methyl-2-phenoxy)titanium dichloride, diphenylmethylene(cyclopentadienyl)(3-phenyl-2-phenoxy)titanium dichloride, diphenylmethylene(cyclopentadienyl)(3-tert-butyldimethylsilyl-5-methyl-2-phenoxy)titanium dichloride, diphenylmethylene(cyclopentadienyl)(3-trimethylsilyl-5-methyl-2-phenoxy)titanium dichloride, diphenylmethylene(cyclopentadienyl)(3-tert-butyl-5-methoxy-2-phenoxy)titanium dichloride, diphenylmethylene(cyclopentadienyl)(3-tert-butyl-5-chloro-2-phenoxy)titanium dichloride, diphenylmethylene(methylcyclopentadienyl)(3,5-dimethyl-2-phenoxy)titanium dichloride, diphenylmethylene(methylcyclopentadienyl)(3-tert-butyl-2-phenoxy)titanium dichloride, diphenylmethylene(methylcyclopentadienyl)(3-tert-butyl-5-methyl-2-phenoxy)titanium dichloride, diphenylmethylene(methylcyclopentadienyl)(3-phenyl-2-phenoxy)titanium dichloride, diphenylmethylene(methylcyclopentadienyl)(3-tert-butyldimethylsilyl-5-methyl-2-phenoxy)titanium dichloride, diphenylmethylene(methylcyclopentadienyl)(3-trimethylsilyl-5-methyl-2-phenoxy)titanium dichloride, diphenylmethylene(methylcyclopentadienyl)(3-tert-butyl-5-methoxy-2-phenoxy)titanium dichloride, diphenylmethylene(methylcyclopentadienyl)(3-tert-butyl-5-chloro-2-phenoxy)titanium dichloride, diphenylmethylene(tert-butylcyclopentadienyl)(3,5-dimethyl-2-phenoxy)titanium dichloride, diphenylmethylene(tert-butylcyclopentadienyl)(3-tert-butyl-2-phenoxy)titanium dichloride, diphenylmethylene(tert-butylcyclopentadienyl)(3-tert-butyl-5-methyl-2-phenoxy)titanium dichloride, diphenylmethylene(tert-butylcyclopentadienyl)(3-phenyl-2-phenoxy)titanium dichloride, diphenylmethylene(tert-butylcyclopentadienyl)(3-tert-butyldimethylsilyl-5-methyl-2-phenoxy)titanium dichloride, diphenylmethylene(tert-butylcyclopentadienyl)(3-trimethylsilyl-5-methyl-2-phenoxy)titanium dichloride, diphenylmethylene(tert-butylcyclopentadienyl)(3-tert-butyl-5-methoxy-2-phenoxy)titanium dichloride, diphenylmethylene(tert-butylcyclopentadienyl)(3-tert-butyl-5-chloro-2-phenoxy)titanium dichloride, diphenylmethylene(tetramethylcyclopentadienyl)(3,5-dimethyl-2-phenoxy)titanium dichloride, diphenylmethylene(tetramethylcyclopentadienyl)(3-tert-butyl-2-phenoxy)titanium dichloride, diphenylmethylene(tetramethylcyclopentadienyl)(3-tert-butyl-5-methyl-2-phenoxy)titanium dichloride, diphenylmethylene(tetramethylcyclopentadienyl)(3-phenyl-2-phenoxy)titanium dichloride, diphenylmethylene(tetramethylcyclopentadienyl)(3-tert-butyldimethylsilyl-5-methyl-2-phenoxy)titanium dichloride, diphenylmethylene(tetramethylcyclopentadienyl)(3-trimethylsilyl-5-methyl-2-phenoxy)titanium dichloride, diphenylmethylene(tetramethylcyclopentadienyl)(3-tert-butyl-5-methoxy-2-phenoxy)titanium dichloride, diphenylmethylene(tetramethylcyclopentadienyl)(3-tert-butyl-5-chloro-2-phenoxy)titanium dichloride, diphenylmethylene(indenyl)(3,5-dimethyl-2-phenoxy)titanium dichloride, diphenylmethylene(indenyl)(3-tert-butyl-2-phenoxy)titanium dichloride, diphenylmethylene(indenyl)(3-tert-butyl-5-methyl-2-phenoxy)titanium dichloride, diphenylmethylene(indenyl)(3-phenyl-2-phenoxy) titanium dichloride, diphenylmethylene(indenyl)(3-tert-butyldimethylsilyl-5-methyl-2-phenoxy)titanium dichloride, diphenylmethylene(indenyl)(3-trimethylsilyl-5-methyl-2-phenoxy)titanium dichloride, diphenylmethylene(indenyl)(3-tert-butyl-5-methoxy-2-phenoxy)titanium dichloride, diphenylmethylene(indenyl)(3-tert-butyl-5-chloro-2-phenoxy)titanium dichloride, diphenylmethylene(fluorenyl)(3,5-dimethyl-2-phenoxy) titanium dichloride, diphenylmethylene(fluorenyl)(3-tert-butyl-2-phenoxy)titanium dichloride, diphenylmethylene (fluorenyl)(3-tert-butyl-5-methyl-2-phenoxy)titanium dichloride, diphenylmethylene(fluorenyl)(3-phenyl-2-phenoxy)titanium dichloride, diphenylmethylene(fluorenyl)(3-tert-butyldimethylsilyl-5-methyl-2-phenoxy)titanium dichloride, diphenylmethylene(fluorenyl)(3-trimethylsilyl-5-methyl-2-phenoxy)titanium dichloride, diphenylmethylene(fluorenyl)(3-tert-butyl-5-methoxy-2-phenoxy)titanium dichloride, diphenylmethylene(fluorenyl)(3-tert-butyl-5-chloro-2-phenoxy)titanium dichloride, compounds obtained by replacing titanium of these exemplified compounds with zirconium and hafnium, compounds obtained by replacing these exemplified chlorides into bromides, iodides, dimethylamides, diethylamides, n-butoxides, and isopropoxides, compounds obtained by replacing (cyclopentadienyl) of the above-exemplified compounds with (dimethylcyclopentadienyl), (trimethylcyclopentadienyl), and (n-butylcyclopentadienyl), and compounds obtained by replacing 3,5-dimethyl-2-phenoxy of the above-exemplified compounds with 2-phenoxy, 3-methyl-2-phenoxy, 3,5-di-tert-butyl-2-phenoxy, 3-phenyl-5-methyl-2-phenoxy, 3-tert-butyldimethylsilyl-2-phenoxy, and 3-trimethylsilyl-2-phenoxy.

The metallocene compound of formula (3) of the invention can be produced by reaction of the silicon-substituted cyclopentadiene compound of formula (1) and the transition metal complex of formula (2) in a solvent containing an aromatic hydrocarbon.

It has been known that the metallocene compound of formula (3) can be obtained by, for example, a method similar to the method (e.g., the above-mentioned Non-Patent Document 1) of causing reaction of a brominated phenol and a base and successively reacting the resulting product with dimethylfulvene, and thereafter with titanium tetrachloride, or the method (e.g., the above-mentioned Non-Patent Document 1) of heating a compound obtained by bonding methoxyphenol and cyclopentadienyltitanium trichloride at 110° C. under reduced pressure, however the technique of the invention is more advantageous in terms of the yield.

The metallocene compound of formula (3) of the invention can be produced also by reacting a substituted cyclopentadiene compound of formula (4) and a base in a solvent containing an aromatic hydrocarbon, successively reacting the resulting reaction product with a halogenated silyl compound of formula (5), and without refining the produced substance, and reacting the resulting substance with a transition metal compound of formula (2).

The base that may be used in these production processes are bases capable of substract a proton from a cyclopentadiene ring, and of which examples are organic alkali metal compounds such as organic lithium compounds, e.g., methyllithium, ethyllithium, n-butyllithium, sec-butyllithium, tert-butyllithium, lithium trimethylsilylacetylide, lithium acetylide, trimethylsilylmethyllithium, vinyllithium, phenyllithium, and allyllithium and the use amount of the base is generally in a range from 0.5 to 5 moles and preferably in a range from 1.1 to 2 moles to 1 mole of the substituted cyclopentadiene compound of formula (4).

The substituted cyclopentadiene compound of formula (4) is obtained, for example, by a method similar to the method (e.g., the above-mentioned Patent Document 1) of causing reaction of a halogenated aryl compound with an organic alkali metal compound or metal magnesium and thereafter successively reaction of the reaction product with a cyclopentadienylidene compound.

Examples of the substituted cyclopentadiene compound of formula (4) are 2-[(cyclopenta-1,4-dienyl)methyl]-1-methoxybenzene, 2-[(cyclopenta-1,4-dienyl)methyl]-1-methoxy-4,6-dimethylbenzene, 2-tert-butyl-6-[(cyclopenta-1,4-dienyl)methyl]-1-methoxy-4-methylbenzene, 6-[(cyclopenta-1,4-dienyl)methyl]-1-methoxy-2-phenylbenzene, 1-tert-butyldimethylsilyl-3-[(cyclopenta-1,4-dienyl)methyl]-2-methoxy-5-methoxybenzene, 3-[(cyclopenta-1,4-dienyl) methyl]-2-methoxy-5-methyl-1-trimethylsilylbenzene, 2-tert-butyl-6-[(cyclopenta-1,4-dienyl)methyl]-1,4-dimethoxybenzene, 3-tert-butyl-1-chloro-5-[(cyclopenta-1,4-dienyl)methyl]-4-methoxybenzene, 2-tert-butyl-6-[(cyclopenta-1,4-dienyl)methyl]-1-methoxybenzene, 2-[1-(cyclopenta-1,4-dienyl)-1-methyl-ethyl]-1-methoxybenzene, 2-[1-(cyclopenta-1,4-dienyl)-1-methyl-ethyl]-1-methoxy-4,6-dimethylbenzene, 6-tert-butyl-2-[1-(cyclopenta-1,4-dienyl)-1-methyl-ethyl]-1-methoxy-4-methylbenzene, 6-[1-(cyclopenta-1,4-dienyl)-1-methyl-ethyl]-1-methoxy-2-phenylbenzene, 1-tert-butyldimethylsilyl-3-[1-(cyclopenta-1,4-dienyl)-1-methyl-ethyl]-2-methoxy-5-methoxybenzene, 3-[1-(cyclopenta-1,4-dienyl)-1-methyl-ethyl]-2-methoxy-5-methyl-1-trimethylsilylbenzene, 6-tert-butyl-2-[1-(cyclopenta-1,4-dienyl)-1-methyl-ethyl]-1,4-dimethoxybenzene, 5-tert-butyl-1-chloro-3-[1-(cyclopenta-1,4-dienyl)-1-methyl-ethyl]-4-methoxybenzene, 6-tert-butyl-2-[1-(cyclopenta-1,4-dienyl)-1-methyl-ethyl]-1-methoxybenzene, 1-methoxy-2-[1-(4-methylcyclopenta-1,4-dienyl)-1-methyl-ethyl]benzene, 1-methoxy-4,6-dimethyl-2-[1-(4-methylcyclopenta-1,4-dienyl)-1-methyl-ethyl]benzene, 6-tert-butyl-1-methoxy-4-methyl-2-[1-(4-methylcyclopenta-1,4-dienyl)-1-methyl-ethyl]benzene, 1-methoxy-6-[1-(4-methylcyclopenta-1,4-dienyl)-1-methyl-ethyl]-2-phenylbenzene, 1-tert-butyldimethylsilyl-2-methoxy-5-methyl-3-[1-(4-methylcyclopenta-1,4-dienyl)-1-methyl-ethyl]benzene, 2-methoxy-5-methyl-3-[1-(4-methylcyclopenta-1,4-dienyl)-1-methyl-ethyl]-1-trimethylsilylbenzene, 6-tert-butyl-1,4-dimethoxy-2-[1-(4-methylcyclopenta-1,4-dienyl)-1-methyl-ethyl]benzene, 5-tert-butyl-1-chloro-4-methoxy-3-[1-(4-methylcyclopenta-1,4-dienyl)-1-methyl-ethyl]benzene, 6-tert-butyl-1-methoxy-2-[1-(4-methylcyclopenta-1,4-dienyl)-1-methyl-ethyl]benzene, 2-[1-(4-tert-butylcyclopenta-1,4-dienyl)-1-methyl-ethyl]-1-methoxybenzene, 2-[1-(4-tert-butylcyclopenta-1,4-dienyl)-1-methyl-ethyl]-1-methoxy-4,6-dimethyl-benzene, 6-tert-butyl-2-[1-(4-tert-butylcyclopenta-1,4-dienyl)-1-methyl-ethyl]-1-methoxy-4-methylbenzene, 6-[1-(4-tert-butylcyclopenta-1,4-dienyl)-1-methyl-ethyl]-1-methoxy-2-phenylbenzene, 1-tert-butyldimethylsilyl-3-[1-(4-tert-butylcyclopenta-1,4-dienyl)-1-methyl-ethyl]-2-methoxy-5-methyl-benzene, 3-[1-(4-tert-butylcyclopenta-1,4-dienyl)-1-methyl-ethyl]-2-methoxy-5-methyl-1-trimethylsilylbenzene, 6-tert-butyl-2-[1-(4-tert-butylcyclopenta-1,4-dienyl)-1-methyl-ethyl]-1,4-dimethoxybenzene, 5-tert-butyl-1-chloro-3-[1-(4-tert-butylcyclopenta-1,4-dienyl)-1-methyl-ethyl]-4-methoxybenzene, 6-tert-butyl-2-[1-(4-tert-butylcyclopenta-1,4-dienyl)-1-methyl-ethyl]-1-methoxybenzene, 1-methoxy-2-[1-(2,3,4,5-tetramethylcyclopenta-1,4-dienyl)-1-methyl-ethyl]benzene, 1-methoxy-4,6-dimethyl-2-[1-(2,3,4,5-tetramethylcyclopenta-1,4-dienyl)-1-methyl-ethyl]benzene, 6-tert-butyl-1-methoxy-4-methyl-2-[1-(2,3,4,5-tetramethylcyclopenta-1,4-dienyl)-1-methyl-ethyl]benzene, 1-methoxy-2-phenyl-6-[1-(2,3,4,5-tetramethylcyclopenta-1,4-dienyl)-1-methyl-ethyl]benzene, 1-tert-butyldimethylsilyl-2-methoxy-5-methyl-3-[1-(2,3,4,5-tetramethylcyclopenta-1,4-dienyl)-1-methyl-ethyl]benzene, 2-methoxy-5-methyl-3-[1-(2,3,4,5-tetramethylcyclopenta-1,4-dienyl)-1-methyl-ethyl]-1-trimethylsilylbenzene, 6-tert-butyl-1,4-dimethoxy-2-[1-(2,3,4,5-tetramethylcyclopenta-1,4-dienyl)-1-methyl-ethyl]benzene, 5-tert-butyl-1-chloro-4-methoxy-3-[1-(2,3,4,5-tetramethylcyclopenta-1,4-dienyl)-1-methyl-ethyl]benzene, 6-tert-butyl-1-methoxy-2-[1-(2,3,4,5-tetramethylcyclopenta-1,4-dienyl)-1-methyl-ethyl]benzene, 2-[1-(cyclopenta-1,4-dienyl)-1-ethyl-propyl]-1-methoxybenzene, 2-[1-(cyclopenta-1,4-dienyl)-1-ethyl-propyl]-1-methoxy-4,6-dimethyl-benzene, 6-tert-butyl-2-[1-(cyclopenta-1,4-dienyl)-1-ethyl-propyl]-1-methoxy-4-methylbenzene, 6-[1-(cyclopenta-1,4-dienyl)-1-ethyl-propyl]-1-methoxy-2-phenylbenzene, 1-tert-butyldimethylsilyl-3-[1-(cyclopenta-1,4-dienyl)-1-ethyl-propyl]-2-methoxy-5-methyl-benzene, 3-[1-(cyclopenta-1,4-dienyl)-1-ethyl-propyl]-2-methoxy-5-methyl-1-trimethylsilylbenzene, 6-tert-butyl-2-[1-(cyclopenta-1,4-dienyl)-1-ethyl-propyl]-1,4-dimethoxybenzene, 5-tert-butyl-1-chloro-3-[1-(cyclopenta-1,4-dienyl)-1-ethyl-propyl]-4-methoxybenzene, 6-tert-butyl-2-[1-(cyclopenta-1,4-dienyl)-1-ethyl-propyl]-1-methoxybenzene, 2-[1-(cyclopenta-1,4-dienyl)-1,1-diphenylmethyl]-1-methoxybenzene, 2-[1-(cyclopenta-1,4-dienyl)-1,1-diphenylmethyl]-1-methoxy-4,6-dimethyl-benzene, 6-tert-butyl-2-[1-(cyclopenta-1,4-dienyl)-1,1-diphenylmethyl]-1-methoxy-4-methylbenzene, 2-[1-(cyclopenta-1,4-dienyl)-1,1-diphenylmethyl]-1-methoxy-6-phenylbenzene, 1-tert-butyldimethylsilyl-3-[1-(cyclopenta-1,4-dienyl)-1,1-diphenylmethyl]-2-methoxy-5-methyl-benzene, 3-[(cyclopenta-1,4-dienyl)-1,1-diphenylmethyl]-2-methoxy-5-methyl-1-trimethylsilylbenzene, 6-tert-butyl-2-[(cyclopenta-1,4-dienyl)-1,1-diphenylmethyl]-1,4-dimethoxybenzene, 5-tert-butyl-1-chloro-3-[(cyclopenta-1,4-dienyl)-1,1-diphenylmethyl]-4-methoxybenzene, 6-tert-butyl-2-[(cyclopenta-1,4-dienyl)-1,1-diphenylmethyl]-1-methoxybenzene, compounds obtained by replacing methoxy of these exemplified compounds with ethoxy, isopropoxy, benzoyloxy, trimethylsilyloxy, tert-butyldimethylsilyloxy, and methoxymethoxy, compounds obtained by replacing cyclopenta-1,4-dienyl of these exemplified compounds with dimethylcyclopenta-1,4-dienyl, trimethylcyclopenta-1,4-dienyl, n-butylcyclopenta-1,4-dienyl, indenyl, and fluorenyl, compounds obtained by replacing 1-methoxybenzene of these exemplified compounds with 1-methoxy-6-methylbenzene, 1-methoxy-4,6-di-tert-butylbenzene, 1-methoxy-4-methyl-6-phenylbenzene, 1-tert-butyldimethylsilyl-2-methoxybenzene, and 2-methoxy-1-trimethylsilylbenzene, and isomers of these exemplified compounds in which the double bond of the cyclopentadiene ring is at different positions.

Examples of the halogenated silyl compound of formula (5) are chlorotrimethylsilane, chlorotriethylsilane, chlorotriisopropylsilane, chlorotri-n-propylsilane, chlorotri-n-butylsilane, chlorotri-sec-butylsilane, chloro-tri-tert-butylsilane, tert-butyldimethylchlorosilane, dimethylphenylchlorosilane, chloromethylsilacyclohexane, chloromethylsilacyclobutane, chloromethylsilacyclopentane, chlorotriphenylsilane, 3-chloropropyldimethylchlorosilane, dichlorodimethylsilane, methyltrichlorosilane, tetrachlorosilane, and compounds obtained by replacing chlorine of these exemplified compounds with fluorine, bromine, and iodine and preferably chlorotrimethylsilane and tert-butyldimethylchlorosilane.

The metallocene compound of formula (3) can be produced in a particularly high yield in a solvent containing an aromatic, hydrocarbon. As the aromatic hydrocarbon is exemplified benzene which may have a substituent such as a halogen atom, a $C_{1-5}$ alkyl, or a $C_{1-5}$ alkoxy and practical examples are benzene, toluene, o-xylene, m-xylene, p-xylene, ethylbenzene, n-propylbenzene, cumene, n-butylbenzene, sec-butylbenzene, isobutylbenzene, tert-butylbenzene, amylbenzene, isoamylbenzene, 2-ethyltoluene, 3-ethyltoluene, 4-ethyltoluene, mesitylene, anisole, 2-methylanisole, 3-methylanisole, 4-methylanisole, phenetole, propyl phenyl ether, butyl phenyl ether, pentyl phenyl ether, chlorobenzene, dichlorobenzene, and trichlorobenzene, preferably benzene, toluene and xylene and particularly preferably toluene. These aromatic hydrocarbon solvents may be used alone while mixtures of the organic solvent containing further one or more organic solvents that are inert to the reaction such as aliphatic hydrocarbon solvents, e.g., pentane, hexane, heptane, octane and the like; ether solvents such as diethyl ether, tetrahydrofuran, 1,4-dioxane or the like; and halogenated solvents such as dichloromethane, dichloroethane or the like may be used. The amount of the aromatic hydrocarbon solvent that may be used is generally in a range of about 1 to 200 parts by weight and preferably in a range of about 3 to 50 parts by weight per 1 part by weight of the silicon-substituted cyclopentadiene compound of formula (1), and the aromatic hydrocarbon solvent may be used as a mixture of organic solvents containing an organic solvent that is inert to the reaction and the aromatic hydrocarbon solvent, preferably in the amount of 50% by weight of the mixture.

The reaction temperature is generally −100° C. to a boiling point of the solvent, preferably −80 to 100° C., more preferably −10 to 100° C., and even more preferably −10 to 60° C.

After completion of the reaction, the metallocene compound of formula (3) can be obtained, for example, by removal of insoluble solid matter and followed by evaporation of the solvent, or it can be obtained from a filtrate after removal of the insoluble matter, which filtrate is obtained by concentration of the reaction mixture. If necessary, the obtained metallocene compound can be purified by conventional method such as recrystallization, sublimation or the like.

The metallocene compound of formula (3) produced by the above-mentioned method can be used for polymerization reaction while being reacted with an activation cocatalyst.

Examples of the activation cocatalyst include compounds such as a zinc compound, an aluminum compound, or a boron compound which may be used commonly in polymerization reaction.

The activation cocatalyst is preferably an aluminum compound and a non-aluminum compound which is coupled with a transition metal to form an ion complex and the compounds may be used alone or in combination for polymerization reaction while being reacted with a metal complex.

INDUSTRIAL APPLICABILITY OF THE INVENTION

The metallocene compound produced by the invention is effective in, for example, polymerization reaction of olefins and has industrial advantage.

EXAMPLES

Hereinafter, the invention will be described more in detail along with Examples, however it is not intended that the invention be limited to the illustrated Examples.

[NMR Measurement Conditions]

Apparatus: JEOL EX 270 model NMR spectrometer or Bruker DPX-300 model NMR spectrometer Sample: 5 mmF tube; sample concentration: 10 mg/0.5 mL (CDCl$_3$ or toluene-d$_8$)

Measurement parameters: 5 mmF probe; MENUF: NON, OBNUC: 1H; times: 256 times

Internal standard: CDCl$_3$ (7.26 ppm), toluene-d$_8$ (2.09 ppm)

Pulse angle: 450

Temperature: room temperature (about 25° C.)

Repeating time (ACQTM+PD): about 7 seconds

[MS Measurement Conditions (EI)]

Apparatus: JMS-AX 505W, manufactured by JEOL Ltd.

Ionization voltage: 70 eV

Ion source temperature: 230° C.

Data processing apparatus: MS-MP 8020D

MASS RANGE: m/z 35-1000

Example 1

Synthesis of isopropylidene(cyclopentadienyl)(3-tert-butyl-5-methyl-2-phenoxy)titanium dichloride Under nitrogen atmosphere, a toluene solution (27 mL) containing titanium tetrachloride (0.67 g, 3.52 mmol) was stirred at −50° C. A solution of 6-tert-butyl-2-[1-(3-trimethylsilylcyclopenta-1,4-dienyl)-1-methyl-ethyl]-1-methoxy-4-methylbenzene (1.26 g, 3.52 mmol) in toluene (10 mL) was added dropwise to the toluene solution. After the mixture was warmed to a room temperature, the solution was heated at 90° C. for 2 hours. After being cooled to a room temperature, the solution was filtered through Celite and the obtained filtrate was concentrated. Hexane was added to the mixture to obtain isopropylidene(cyclopentadienyl)(3-tert-butyl-5-methyl-2-phenoxy)titanium dichloride as a brown solid (0.68 g, yield 49.7%).

$^1$H-NMR (CDCl$_3$, d(ppm)): 1.42 (s, 9H, Ar-tBu), 1.60 (s, 6H, Me$_2$C), 2.39 (s, 3H, Ar-Me), 6.12 (t, J=2.7 Hz, 2H, Cp), 6.97 (t, J=2.7 Hz, 2H, Cp), 7.22 (s, 1H, Ar), 7.26 (s, 1H, Ar)

Mass spectrum (EI, m/z): 386 (M$^+$), 371, 335

Example 2

In nitrogen atmosphere, 6-tert-butyl-2-[1-(cyclopenta-1,4-dienyl)-1-methyl-ethyl]-1-methoxy-4-methylbenzene (1.00 g, 3.52 mmol) was dissolved in toluene (30 mL) and cooled to 10° C. After that, a solution of n-butyllithium in hexane (2.73 mL, 1.58 M, 4.31 mmol) was added dropwise to the obtained toluene solution and stirred at 50° C. for 1 hour. After the reaction mixture was cooled to 0° C., a solution of chlorotrimethylsilane (0.47 g, 4.31 mmol) in toluene (5.78 mL) was added dropwide and stirred at 50° C. for 1 hour. After the reaction mixture was cooled to −50° C., a solution obtained by dissolving titanium tetrachloride (0.82 g, 4.31 mmol) in toluene (5.78 mL) was added dropwise and the mixture was heated to a room temperature. After that, the mixture was heated at 90° C. for 2 hours and successively cooled to a room temperature and the reaction mixture was filtered through Celite and the obtained filtrate was concentrated. Hexane was added to the mixture to obtain isopropylidene(cyclopentadienyl)(3-tert-butyl-5-methyl-2-phenoxy)titanium dichloride as a brown solid (0.80 g, yield 58.8%).

Example 3

The reaction was carried out in the same manner as Example 2, except that 0.52 g (4.74 mmol) of chlorotrimethylsilane was used to obtain isopropylidene(cyclopentadienyl)(3-tert-butyl-5-methyl-2-phenoxy)titanium dichloride as a brown solid (0.73 g, yield 53.6%).

Example 4

The reaction was carried out in the same manner as Example 3, except that the addition temperature of titanium tetrachloride was changed to 0° C. and the heating temperature after addition of titanium tetrachloride was changed to 70° C. to obtain isopropylidene(cyclopentadienyl)(3-tert-butyl-5-methyl-2-phenoxy)titanium dichloride as a brown solid (0.65 g, yield 48.1%).

Example 5

The reaction was carried out in the same manner as Example 3, except that the addition temperature of titanium tetrachloride was changed to 0° C. and the heating temperature after addition of titanium tetrachloride was changed to 50° C. to obtain isopropylidene(cyclopentadienyl)(3-tert-butyl-5-methyl-2-phenoxy)titanium dichloride as a brown solid (0.77 g, yield 56.5%).

Example 6

In nitrogen atmosphere, 6-tert-butyl-2-[1-(cyclopenta-1,4-dienyl)-1-methyl-ethyl]-1-methoxy-4-methylbenzene (1.00 g, 3.52 mmol) was dissolved in toluene (30 mL) and cooled to 0° C. After that, a solution of n-butyllithium in hexane (2.80 mL, 1.58 M, 4.42 mmol) was added dropwise to the obtained toluene solution and stirred at 50° C. for 1 hour. After the reaction mixture was cooled to 0° C., a solution containing chlorotrimethylsilane (0.48 g, 4.42 mmol) in toluene (5.78 mL) was added dropwise and stirred at 50° C. for 1 hour. After the reaction mixture was cooled to 0° C., a solution obtained by dissolving titanium tetrachloride (0.84 g, 4.42 mmol) in toluene (5.78 mL) was added dropwise and the mixed solution was warmed to a room temperature. After that, the solution was heated at 50° C. for 2 hours and successively cooled to a room temperature and the reaction mixture was filtered through Celite and the obtained filtrate was concentrated. The obtained filtrate was subjected to $^1$H-NMR analysis (toluene-d$_8$) using dibromoethane as an internal standard to measure the content of isopropylidene(cyclopentadienyl)(3-tert-butyl-5-methyl-2-phenoxy)titanium dichloride (0.89 g, yield 65.8%).

$^1$H-NMR (toluene-d$_8$, d(ppm)): 1.23 (s, 6H, Me$_2$C), 1.52 (s, 9H, Ar-tBu), 2.09 (s, 3H, Ar-Me), 5.47 (t, J=2.7 Hz, 2H, Cp), 6.29 (t, J=2.7 Hz, 2H, Cp), 6.97-7.09 (2H, Ar)

Example 7

The reaction was carried out in the same manner as Example 6, except that 1.01 g (5.30 mmol) of titanium tetrachloride was used. The content of isopropylidene(cyclopentadienyl)(3-tert-butyl-5-methyl-2-phenoxy)titanium dichloride was confirmed by ¹H-NMR analysis (0.94 g, yield 69.2%).

Example 8

The reaction was carried out in the same manner as Example 6, except that the method was changed by addition of the reaction mixture to the titanium tetrachloride solution. The content of isopropylidene(cyclopentadienyl)(3-tert-butyl-5-methyl-2-phenoxy)titanium dichloride was confirmed by ¹H-NMR analysis (0.84 g, yield 61.8%).

Example 9

The reaction was carried out in the same manner as Example 6, except that the amount of toluene to dissolve 6-tert-butyl-2-[1-(cyclopenta-1,4-dienyl)-1-methyl-ethyl]-1-methoxy-4-methylbenzene was changed to 15 mL. The content of isopropylidene(cyclopentadienyl)(3-tert-butyl-5-methyl-2-phenoxy)titanium dichloride was confirmed by ¹H-NMR analysis (0.85 g, yield 62.7%).

Example 10

The reaction was carried out in the same manner as Example 9, except that neat chlorotrimethylsilane was added dropwise as it was without being dissolved in toluene. The content of isopropylidene(cyclopentadienyl)(3-tert-butyl-5-methyl-2-phenoxy)titanium dichloride was confirmed by ¹H-NMR analysis (0.93 g, yield 69.0%).

Example 11

The reaction was carried out in the same manner as Example 10, except that addition temperature of chlorotrimethylsilane was changed to 50° C. The content of isopropylidene(cyclopentadienyl)(3-tert-butyl-5-methyl-2-phenoxy)titanium dichloride was confirmed by ¹H-NMR analysis (0.87 g, yield 63.8%).

Example 12

The reaction was carried out in the same manner as Example 11, except that 1.01 g (5.30 mmol) of titanium tetrachloride was used. The content of isopropylidene(cyclopentadienyl)(3-tert-butyl-5-methyl-2-phenoxy)titanium dichloride was confirmed by ¹H-NMR analysis (1.02 g, yield 75.2%).

Example 13

The reaction was carried out in the same manner as Example 7, except that 0.67 g (3.55 mmol) of titanium tetrachloride was used. The content of isopropylidene(cyclopentadienyl)(3-tert-butyl-5-methyl-2-phenoxy)titanium dichloride was confirmed by ¹H-NMR analysis (0.65 g, yield 47.7%).

Example 14

The reaction was carried out in the same manner as Example 7, except that 0.75 g (3.97 mmol) of titanium tetrachloride was used. The content of isopropylidene(cyclopentadienyl)(3-tert-butyl-5-methyl-2-phenoxy)titanium dichloride was confirmed by ¹H-NMR analysis (0.67 g, yield 49.6%).

Example 15

The reaction was carried out in the same manner as Example 7, except that 0.84 g (4.42 mmol) of titanium tetrachloride was used. The content of isopropylidene(cyclopentadienyl)(3-tert-butyl-5-methyl-2-phenoxy)titanium dichloride was confirmed by ¹H-NMR analysis (0.89 g, yield 65.8%).

Example 16

The reaction was carried out in the same manner as Example 7, except that 0.92 g (4.88 mmol) of titanium tetrachloride was used. The content of isopropylidene(cyclopentadienyl)(3-tert-butyl-5-methyl-2-phenoxy)titanium dichloride was confirmed by ¹H-NMR analysis (0.88 g, yield 64.5%).

Example 17

The reaction was carried out in the same manner as Example 7, except that 1.10 g (5.76 mmol) of titanium tetrachloride was used. The content of isopropylidene(cyclopentadienyl)(3-tert-butyl-5-methyl-2-phenoxy)titanium dichloride was confirmed by ¹H-NMR analysis (0.94 g, yield 69.4%).

Example 18

The reaction was carried out in the same manner as Example 7, except that 1.18 g (6.18 mmol) of titanium tetrachloride was used. The content of isopropylidene(cyclopentadienyl)(3-tert-butyl-5-methyl-2-phenoxy)titanium dichloride was confirmed by ¹H-NMR analysis (0.92 g, yield 68.1%).

Example 19

Synthesis of isopropylidene(cyclopentadienyl)(3-tert-butyl-5-methyl-2-phenoxy)zirconium dichloride In nitrogen atmosphere, 6-tert-butyl-2-[1-(cyclopenta-1,4-dienyl)-1-methyl-ethyl]-1-methoxy-4-methylbenzene (3.00 g, 10.55 mmol) was dissolved in toluene (43 mL) and cooled to 0° C. After that, a solution of n-butyllithium in hexane (9.48 mL, 1.58 M, 14.98 mmol) was added dropwise to the obtained toluene solution and stirred at 50° C. for 1 hour. chlorotrimethylsilane (1.63 g, 14.98 mmol) was added dropwise and stirred at 50° C. for 1 hour. After the reaction mixture was cooled to 0° C., the reaction mixture was added dropwise to a suspension of zirconium tetrachloride (4.18 g, 17.93 mmol) in toluene (9 mL) and the mixture was heated to a room temperature. After that, the mixture was heated at 60° C. for 2 hours and successively cooled to a room temperature and the reaction mixture was filtered through Celite and the obtained filtrate was concentrated to obtain isopropylidene(cyclopentadienyl)(3-tert-butyl-5-methyl-2-phenoxy)zirconium dichloride as a brown solid.

The obtained mixture was subjected to ¹H-NMR analysis using dibromoethane as an internal standard to measure the content of isopropylidene(cyclopentadienyl)(3-tert-butyl-5-methyl-2-phenoxy)zirconium dichloride (0.28 g, yield 6.2%).

$^1$H-NMR (CDCl$_3$, d(ppm)): 1.41 (s, 9H, Ar-tBu), 1.59 (s, 6H, Me$_2$C), 2.40 (s, 3H, Ar-Me), 6.10 (t, J=2.7 Hz, 2H, Cp), 6.80 (t, J=2.7 Hz, 2H, Cp), 7.20 (s, 1H, Ar), 7.28 (s, 1H, Ar)

Mass spectrum (EI, m/z): 430 (M$^+$), 415, 377

Example 20

Synthesis of isopropylidene(cyclopentadienyl)(3-tert-butyl-5-methyl-2-phenoxy)hafnium dichloride In nitrogen atmosphere, 6-tert-butyl-2-[1-(cyclopenta-1,4-dienyl)-1-methyl-ethyl]-1-methoxy-4-methylbenzene (3.00 g, 10.55 mmol) was dissolved in toluene (43 mL) and cooled to 0° C. After that, a solution of n-butyllithium solution in hexane (9.48 mL, 1.58 M, 14.98 mmol) was added dropwise to the obtained toluene solution and stirred at 50° C. for 1 hour chlorotrimethylsilane (1.63 g, 14.98 mmol) was added dropwise and stirred at 50° C. for 1 hour. After the reaction mixture was cooled to 0° C., the reaction mixture was added dropwise to a suspension of hafnium tetrachloride (5.74 g, 17.93 mmol) in toluene (9 mL) and the mixture was warmed to a room temperature. After that, the solution was heated at 60° C. for 2 hours and successively cooled to a room temperature and the reaction mixture was filtered through Celite and the obtained filtrate was concentrated to obtain isopropylidene (cyclopentadienyl)(3-tert-butyl-5-methyl-2-phenoxy) hafnium dichloride as a brown solid. The obtained mixture was subjected to $^1$H-NMR analysis using dibromoethane as an internal standard to measure the content of isopropylidene (cyclopentadienyl)(3-tert-butyl-5-methyl-2-phenoxy) hafnium dichloride (3.61 g, yield 66.1%).

$^1$H-NMR (CDCl$_3$, d(ppm)): 1.38 (s, 9H, Ar-tBu), 1.60 (s, 6H, Me$_2$C), 2.38 (s, 3H, Ar-Me), 6.10 (t, J=2.7 Hz, 2H, Cp), 6.70 (t, J=2.7 Hz, 2H, Cp), 7.10 (s, 1H, Ar), 7.21 (s, 1H, Ar)

Mass spectrum (EI, m/z): 518 (M$^+$), 503, 467

Comparative Example 1

In nitrogen atmosphere, 6-tert-butyl-2-[1-(cyclopenta-1,4-dienyl)-1-methyl-ethyl]-1-methoxy-4-methylbenzene (1.00 g, 3.52 mmol) was dissolved in toluene (35 mL) and cooled to 0° C. After that, a solution of n-butyllithium in hexane (2.89 mL, 1.58 M, 4.57 mmol) was added dropwise to the obtained toluene solution and stirred at 50° C. for 4 hours. After the reaction mixture was cooled to −50° C., a solution of titanium tetrachloride (0.67 g, 3.52 mmol) in toluene (8.09 mL) was added dropwise to the reaction mixture and the mixture was heated to a room temperature. After that, the mixture was heated at 90° C. for 2 hours and successively cooled to a room temperature and the reaction mixture was filtered through Celite and the obtained filtrate was concentrated. Hexane was added to the obtained filtrate to obtain isopropylidene(cyclopentadienyl)(3-tert-butyl-5-methyl-2-phenoxy)titanium dichloride as a brown solid (0.46 g, yield 33.6%)

Comparative Example 2

In nitrogen atmosphere, 6-tert-butyl-2-[1-(cyclopenta-1,4-dienyl)-1-methyl-ethyl]-1-methoxy-4-methylbenzene (1.00 g, 3.52 mmol) was dissolved in toluene (25 mL) and cooled to 0° C. After that, a solution of n-butyllithium in hexane (2.80 mL, 1.58 M, 4.42 mmol) was added dropwise to the obtained toluene solution and stirred at 50° C. for 1 hour. After the reaction mixture was cooled to 0° C., a solution of titanium tetrachloride (0.84 g, 3.52 mmol) in toluene (11.56 mL) was added dropwise to the reaction mixture and the mixture was heated to a room temperature. After that, the mixture was heated at 50° C. for 2 hours, and successively cooled to a room temperature and the reaction mixture was filtered through Celite and the obtained filtrate was concentrated. The concentrated filtrate was analyzed by $^1$H-NMR to find it was complicated mixture and production of isopropylidene(cyclopentadienyl)(3-tert-butyl-5-methyl-2-phenoxy)titanium dichloride was slight (0.06 g, yield 4.2%)

What is claimed is:

1. A process for producing a metallocene compound of formula (3);

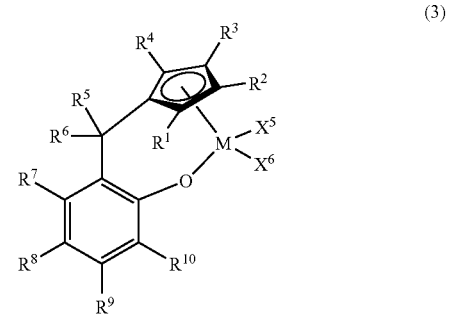

(3)

wherein R$^1$, R$^2$, R$^3$ and R$^4$ independently denote a hydrogen atom, a halogen atom, a substituted or unsubstituted C$_{1-20}$ alkyl, a substituted or unsubstituted C$_{6-20}$ aryl, or a substituted or unsubstituted C$_{7-20}$ aralkyl;

R$^5$, R$^6$, R$^7$, R$^8$, and R$^9$ independently denote a hydrogen atom, a halogen atom, a substituted or unsubstituted C$_{1-20}$ alkyl, a substituted or unsubstituted C$_{1-20}$ alkoxy, a substituted or unsubstituted C$_{6-20}$ aryl, a substituted or unsubstituted C$_{6-20}$ aryloxy, a substituted or unsubstituted C$_{7-20}$ aralkyl, a substituted or unsubstituted C$_{7-20}$ aralkyloxy, a silyl substituted with a substituted or unsubstituted C$_{1-20}$ hydrocarbon group, a silyloxy substituted with a substituted or unsubstituted C$_{1-20}$ hydrocarbon group, or an amino substituted with a substituted or unsubstituted C$_{1-20}$ hydrocarbon group;

R$^{10}$ denotes a halogen atom, a substituted or unsubstituted C$_{1-20}$ alkyl, a substituted or unsubstituted C$_{1-20}$ alkoxy, a substituted or unsubstituted C$_{6-20}$ aryl, a substituted or unsubstituted C$_{6-20}$ aryloxy, a substituted or unsubstituted C$_{7-20}$ aralkyl, a substituted or unsubstituted C$_{7-20}$ aralkyloxy, a silyl substituted with a substituted or unsubstituted C$_{1-20}$ hydrocarbon group, a silyloxy substituted with a substituted or unsubstituted C$_{1-20}$ hydrocarbon group, or an amino substituted with a substituted or unsubstituted C$_{1-20}$ hydrocarbon group;

M denotes a transition metal atom of Group 4 of the Periodic Table;

X$^5$ and X$^6$ may be same or different and independently denote a hydrogen atom, a halogen atom, a substituted or unsubstituted C$_{1-20}$ alkyl, a substituted or unsubstituted C$_{1-20}$ alkoxy, a substituted or unsubstituted C$_{6-20}$ aryl, a substituted or unsubstituted C$_{6-20}$ aryloxy, a substituted or unsubstituted C$_{7-20}$ aralkyl, a substituted or unsubstituted C$_{7-20}$ aralkyloxy, or an amino substituted with a substituted or unsubstituted $C_{1-20}$ hydrocarbon group; each neighboring groups of $R^1$, $R^2$, $R^3$ and $R^4$ may be optionally bonded to each other to form a ring;

$R^5$ and $R^6$ may be bonded to each other to form a ring; and each neighboring groups of $R^7$, $R^8$, $R^9$ and $R^{10}$ may be optionally bonded to each other to form a ring, which process comprises reacting a silicon-substituted cyclopentadiene compound of formula (1);

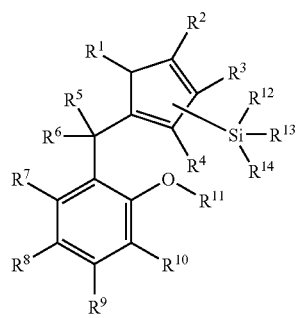

(1)

wherein $R^1$ to $R^{10}$ independently denote same as described above; $R^{11}$ denotes a substituted or unsubstituted hydrocarbon group or a tri-substituted silyl;

$R^{12}$, $R^{13}$ and $R^{14}$ independently denote a halogen atom or a substituted or unsubstituted hydrocarbon group; two or three of $R^{12}$, $R^{13}$, and $R^{14}$ may be bonded one another to form a ring; silicon may be bonded with any one of carbon atoms of the cyclopentadiene ring; and the position of the double bonds of the cyclopentadiene ring may be at optional positions, with a transition metal compound of formula (2);

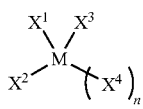

(2)

wherein M denotes same as described above;

$X^1$, $X^2$, $X^3$, and $X^4$ may be same or different and independently denote a hydrogen atom, a halogen atom, a substituted or unsubstituted $C_{1-20}$ alkyl, a substituted or unsubstituted $C_{1-20}$ alkoxy, a substituted or unsubstituted $C_{6-20}$ aryl, a substituted or unsubstituted $C_{6-20}$ aryloxy, a substituted or unsubstituted $C_{7-20}$ aralkyl, a substituted or unsubstituted $C_{7-20}$ aralkyloxy, or an amino substituted with a substituted or unsubstituted $C_{1-20}$ hydrocarbon group; and n denotes 0 or 1, in a solvent containing an aromatic hydrocarbon.

2. A process for producing a metallocene compound of formula (3) according to claim 1, which comprises reacting a substituted cyclopentadiene compound of formula (4);

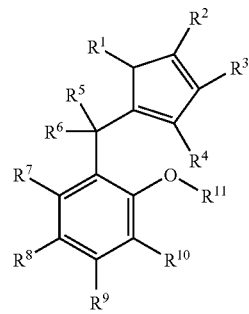

(4)

wherein $R^1$, $R^2$, $R^3$, $R^4$, $R^5$, $R^6$, $R^7$, $R^8$, $R^9$, $R^{10}$, and $R^{11}$ independently denote the same as described in claim 1 and the double bonds of the cyclopentadiene ring may be at optional positions, with a base in a solvent containing an aromatic hydrocarbon, reacting the resulting with a silyl halide compound of formula (5);

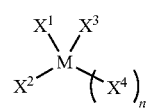

(5)

wherein $R^{12}$, $R^{13}$, and $R^{14}$ independently denote the same as described in claim 1, and Y denotes a halogen atom, and reacting the resulting product, without refining, with a transition metal compound of formula (2);

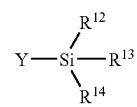

(2)

wherein M, $X^1$, $X^2$, $X^3$, $X^4$, and n independently denote the same as defined in claim 1.

3. The production process according to claim 1 or 2, wherein the aromatic hydrocarbon is benzene or substituted benzene having, as a substituent, a halogen atom, a $C^{1-5}$ alkyl, or a $C^{1-5}$ alkoxy.

4. The production process according to claim 1, wherein the reaction of the silicon-substituted cyclopentadiene compound of formula (1) with the transition metal compound of formula (2) is carried out at a reaction temperature in a range from $-10°$ C. to $100°$ C.

5. The production process according to claim 1, wherein the transition metal compound of formula (2) is titanium tetrachloride and the halogenated silyl compound of formula (5) is chlorotrimethylsilane.

6. The production process according to claim 1, wherein 1.1 moles or more of the transition metal compound of formula (2) is used per 1 mole of the silicon-substituted cyclopentadiene compound of formula (1).

7. The production process according to claim 2, wherein 1.1 moles or more of the transition metal compound of formula (2) is used per 1 mole of the substituted cyclopentadiene compound of formula (4).

* * * * *